(12) United States Patent
Yokomise et al.

(10) Patent No.: US 7,530,947 B2
(45) Date of Patent: May 12, 2009

(54) LESION PORTION DETERMINING METHOD OF INFRARED OBSERVING SYSTEM

(75) Inventors: Hiroyasu Yokomise, Kagawa (JP); Yasumichi Yamamoto, Kagawa (JP); Cheng-Long Huang, Kagawa (JP); Eiichi Hayashi, Kagawa (JP); Kotaro Kameyama, Kagawa (JP); Dage Liu, Kagawa (JP); Taku Okamoto, Kagawa (JP); Masashi Gotoh, Kagawa (JP)

(73) Assignee: Olympus Corporation, Tokyo (JP)

( * ) Notice: Subject to any disclaimer, the term of this patent is extended or adjusted under 35 U.S.C. 154(b) by 926 days.

(21) Appl. No.: 10/856,021

(22) Filed: May 28, 2004

(65) Prior Publication Data
US 2005/0267374 A1    Dec. 1, 2005

(51) Int. Cl.
*A61B 1/06* (2006.01)
*A61B 6/00* (2006.01)

(52) U.S. Cl. .................... 600/160; 600/475
(58) Field of Classification Search ............ 600/109, 600/160, 178, 181, 473–480; 348/68–70
See application file for complete search history.

(56) References Cited

U.S. PATENT DOCUMENTS

| | | | | |
|---|---|---|---|---|
| 4,961,110 A | * | 10/1990 | Nakamura | 348/70 |
| 5,187,572 A | * | 2/1993 | Nakamura et al. | 348/68 |
| 5,255,087 A | * | 10/1993 | Nakamura et al. | 348/71 |
| 5,699,798 A | * | 12/1997 | Hochman et al. | 600/420 |
| 6,293,911 B1 | * | 9/2001 | Imaizumi et al. | 600/160 |
| 2004/0158228 A1 | * | 8/2004 | Perkins et al. | 604/514 |

OTHER PUBLICATIONS

Gotoh, Masahashi, et al., "Development of a canine model of pulmonary emphysema and imaging of the emphysematous lung with infrared thoracoscopy", The Journal of Thoracic and Cardiovascular Surgery, pp. 1916-1921, Dec. 2003, vol. 126, No. 6.

* cited by examiner

*Primary Examiner*—John P Leubecker
*Assistant Examiner*—Philip R Smith
(74) *Attorney, Agent, or Firm*—Scully, Scott, Murphy & Presser, P.C.

(57) ABSTRACT

A lesion portion determining method of an infrared observing system includes at least an observing apparatus. The observing apparatus includes a light source device which radiates light of a first wavelength band including a wavelength of 805 nm and light of a second wavelength band including a wavelength longer than 805 nm, an image pick-up device which picks up an image of the first wavelength band and an image of the second wavelength band of an object irradiated by the light radiated from the light source device, display means which displays, as any color component of red, green, and blue, the image of the first wavelength band and the image of the second wavelength band that are picked-up by the image pick-up device. The lesion portion determining method includes a step of administering an infrared absorbing pigment to a patient, and a step of observing a visible range of the infrared absorbing pigment by the observing apparatus.

42 Claims, 17 Drawing Sheets

FIG.13

| |
|---|
| LEVEL-7 COLOR-TONE ADJUSTING COEFFICIENT |
| LEVEL-6 COLOR-TONE ADJUSTING COEFFICIENT |
| LEVEL-5 COLOR-TONE ADJUSTING COEFFICIENT |
| LEVEL-4 COLOR-TONE ADJUSTING COEFFICIENT |
| LEVEL-3 COLOR-TONE ADJUSTING COEFFICIENT |
| LEVEL-2 COLOR-TONE ADJUSTING COEFFICIENT |
| LEVEL-1 COLOR-TONE ADJUSTING COEFFICIENT |
| INFRARED COLOR-TONE ADJUSTING LEVEL (FOR SIGNAL R) |
| INFRARED COLOR-TONE ADJUSTING LEVEL (FOR SIGNAL G) |
| INFRARED COLOR-TONE ADJUSTING LEVEL (FOR SIGNAL B) |
| VISIBLE COLOR-TONE ADJUSTING LEVEL (FOR SIGNAL R) |
| VISIBLE COLOR-TONE ADJUSTING LEVEL (FOR SIGNAL G) |
| VISIBLE COLOR-TONE ADJUSTING LEVEL (FOR SIGNAL B) |
| INFRARED STRUCTURE EMPHASIZING LEVEL |
| VISIBLE STRUCTURE EMPHASIZING LEVEL |
| INFRARED PIGMENT EMPHASIZING LEVEL |
| VISIBLE PIGMENT EMPHASIZING LEVEL |
| B-CHANNEL VISIBLE COLOR-BALANCE CORRECTING COEFFICIENT (FOR SIGNAL R) |
| B-CHANNEL VISIBLE COLOR-BALANCE CORRECTING COEFFICIENT (FOR SIGNAL G) |
| B-CHANNEL VISIBLE COLOR-BALANCE CORRECTING COEFFICIENT (FOR SIGNAL B) |
| A-CHANNEL INFRARED COLOR-BALANCE CORRECTING COEFFICIENT (FOR SIGNAL R) |
| A-CHANNEL INFRARED COLOR-BALANCE CORRECTING COEFFICIENT (FOR SIGNAL G) |
| A-CHANNEL INFRARED COLOR-BALANCE CORRECTING COEFFICIENT (FOR SIGNAL B) |
| A-CHANNEL VISIBLE COLOR-BALANCE CORRECTING COEFFICIENT (FOR SIGNAL R) |
| A-CHANNEL VISIBLE COLOR-BALANCE CORRECTING COEFFICIENT (FOR SIGNAL G) |
| A-CHANNEL VISIBLE COLOR-BALANCE CORRECTING COEFFICIENT (FOR SIGNAL B) |

[ICG OBSERVED JUST BELOW PULMONARY PLEURA]

NORMAL PULMONARY TISSUE OF DOG

H.E. ×40

PULMONARY TISSUE IMAGE
AFTER 18 DAYS OF PPE ABSORPTION

H.E. ×100

PULMONARY TISSUE IMAGE
AFTER 0 DAY OF PPE INJECTION

H.E. ×100

PULMONARY TISSUE IMAGE
AFTER 33 DAYS OF PPE INJECTION

H.E. ×100

LESION PORTION DETERMINING METHOD OF INFRARED OBSERVING SYSTEM

BACKGROUND OF THE INVENTION

1. Field of the Invention

The present invention relates to a lesion portion determining method of an infrared observing system, and more particularly, to a method for determining the lesion portion in the body cavity by using an infrared observing system for observing the body cavity with infrared rays. Further, particularly, the present invention relates to a lesion portion determining method of an infrared observing system which can identify the lesion portion of the ischemic disease by capturing bloodflow information of the living body with image pick-up means in the infrared observing system and by displaying the captured information, and can easily perform the surgical treatment.

2. Description of the Related Art

Recently, an endoscopic surgical operation is widespread by inserting an endoscope in the body cavity such as the abdominal cavity and thoracic cavity for the surgical operation. An endoscope apparatus used for the above-mentioned endoscopic surgical operation includes an electronic endoscope using an image pick-up device such as a CCD (Charge Coupled Device).

A conventional electronic endoscope displays a clear moving image in realtime on a color monitor. Therefore, the conventional electronic endoscope has been recently widespread. An endoscopic image is captured by the electronic endoscope and then is displayed on the monitor via predetermined signal processing. In the normal case, for the endoscopic image, visible light is used as observing light so that an observed image is close to a result of direct viewing.

An endoscope monitor receives four signals comprising a synchronous signal and a signal R, a signal G, and a signal B indicating a red component R, a green component G, and blue component B. Mainly, a CRT (Cathode Ray Tube) or LCD (Liquid Crystal Display) device displays the signals R, G, and B corresponding to phosphor dots which generate red, green, and blue light.

In the above-mentioned endoscopic surgical operation, the open surgery, which is conventionally operated under the celiotomy or thoracotomy, is performed by a predetermined endoscope system and a dedicated therapeutic instrument (operation tool) used for the endoscopic surgical operation. Advantageously, the invasiveness to a patient is suppressed.

Specifically, in the laparoscopic operation, the operation is accomplished only by opening a plurality of (three or four) holes corresponding to the size of $\phi 5$ mm to $\phi 12$ mm to insert a laparoscope in the abdominal wall. Therefore, as compared with the conventional open surgery, a so-called patient QOL (Quality Of Life) is excessively improved, e.g., the pain reduction after the operation, reduction of a period of admission to hospital, and cosmetic point.

The endoscopic operation is used for many diseases. In the thoracoscopic operation, the endoscopic operation is used for the emphysema, the pneumothorax, and the heart disease. In the laparoscopic operation, the endoscopic operation is used for the cholecystectomy or the operation of the digestive organ such as the stomach or the large intestine. The endoscopic operation is applied to various fields of diseases.

An infrared observing system disclosed in Japanese Unexamined Patent Application Publication No. 2000-41942 comprises: light source means which radiates light having a first wavelength band with a wavelength of 805 nm and light having a second wavelength band without a wavelength of 805 nm; image pick-up means which picks up an image having the first wavelength band and an image having the second wavelength band of an object which is irradiated by the light radiated by the light source means; and a display device which displays the image having the first wavelength band picked-up by the image pick-up means as the green component and displays the image having the second wavelength band as at least one of the red component and the blue component. With the above-mentioned structure, the reflected light having the second wavelength band can be observed with high contrast.

However, the endoscopic operation is a complicated treatment because an operator cannot directly touch the affected part and thus there is no tactile sensation. Further, as compared with the case in which the operator directly observes the affected part, it is pointed that the difference from the open surgery, in the resolution of a display image or stereoscopic sense causes difficulties. Particularly, the artery beating cannot be recognized by the tactile sensation for the bloodflow information in the field of view and thus the bloodflow rate on the peripheral side is not evaluated. The presentation of the information to the operator is a serious subject to be solved.

SUMMARY OF THE INVENTION

According to the present invention, a lesion portion determining method applied to an infrared observing system which includes at least an observing apparatus. The observing apparatus includes: a light source device which radiates light of a first wavelength band including a wavelength of 805 nm and light of a second wavelength band including no wavelength of 805 nm and a wavelength longer than it; an image pick-up device which picks up an image of the first wavelength band and an image of the second wavelength band of an object irradiated by the light radiated from the light source device; display means which displays, as any color component of red, green, and blue, the image of the first wavelength band and the image of the second wavelength band, respectively, that are picked-up by the image pick-up device. The lesion portion determining method includes: a step of administering an infrared absorbing pigment to a patient; and a step of observing a visualization range of the infrared absorbing pigment by the observing apparatus.

The advantages of the present invention will be obvious by the following detailed description.

BRIEF DESCRIPTION OF THE DRAWINGS

FIG. 13 is a diagram showing an internal memory map of a CPU;

DETAILED DESCRIPTION OF THE PREFERRED EMBODIMENTS

Figure 1:
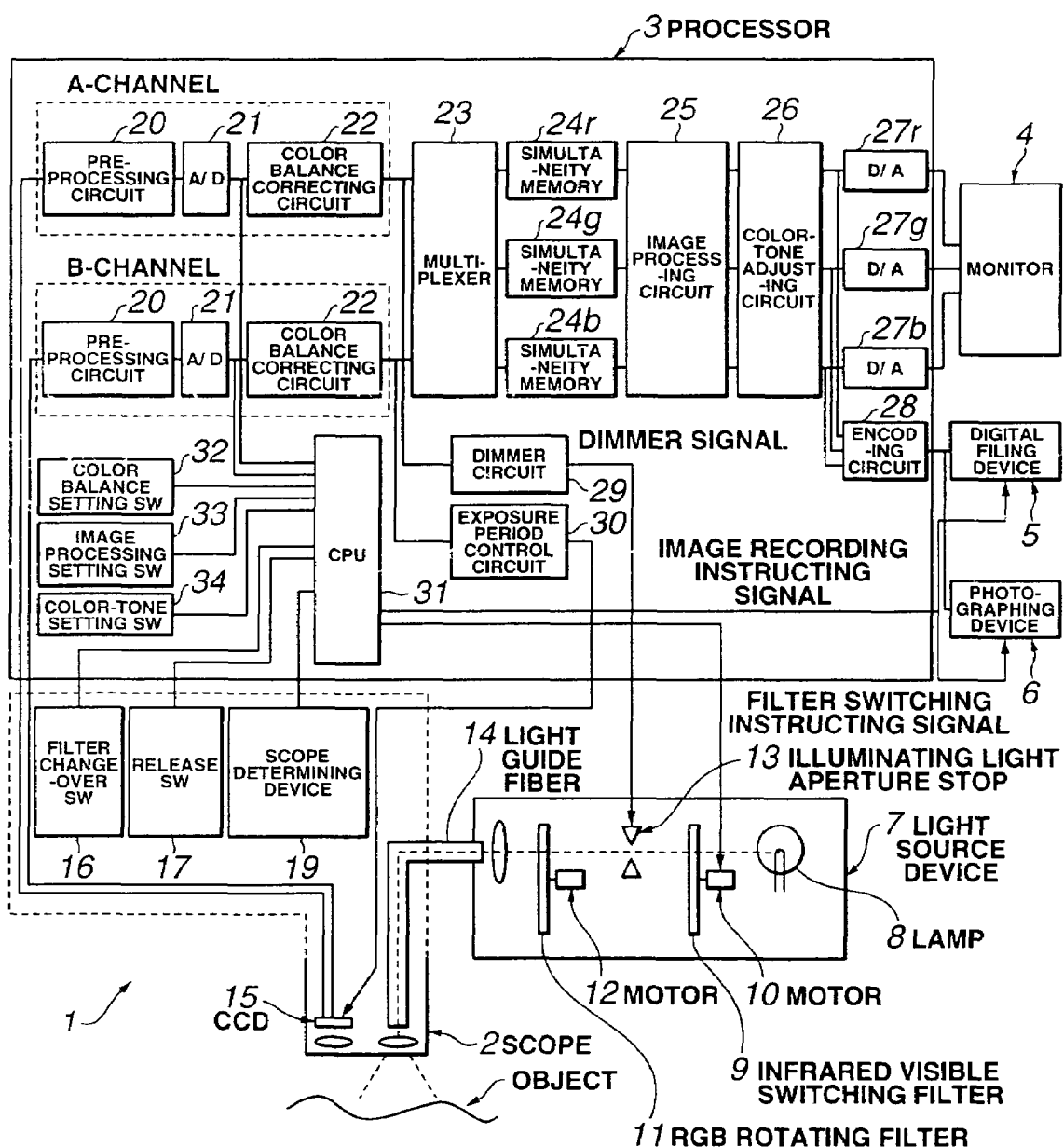
FIG. 1 is a block diagram showing the entire structure of an infrared observing system according to the present invention.

Referring to FIG. 1, an endoscope apparatus 1 included in an infrared observing system according to an embodiment of the present invention comprises: a light source device 7, as light source means, which generates illuminating luminous flux for observation; a scope 2 which is inserted in the body cavity; a processor 3 which receives an image signal captured by an image pick-up device (CCD) 15 arranged to the scope 2 and performs predetermined signal processing; a monitor 4, as a display device, which receives an image display signal outputted from the processor 3 and displays the image; a digital filing device 5 which records a digital image signal; and a photographing device 6 which records the image as a photograph.

The light source device 7 comprises: a lamp 8 as an illuminating member such as an xenon lamp for radiating light; an infrared/visible switching filter 9 which is arranged onto an illuminating optical path of the lamp 8 and limits the transmitting wavelength; a motor 10 which drives the switching of the infrared/visible switching filter 9; an RGB rotating filter 11 having a plurality of filters for limiting the wavelength band of the transmitting light; a motor 12 which drives the rotation of the RGB rotating filter 11; an illuminating light aperture stop 13 which limits the illuminating light amount of the lamp 8; and the like.

The scope 2 comprises: a light guide fiber 14 which transmits the illuminating light from the light source device 7 to the distal portion of the scope 2; an image pick-up device including the solid-state image pick-up device (hereinafter, abbreviated to an image pick-up device) 15 such as a CCD (Charge Coupled Device), constituting image pick-up means, which picks up the light from an object; a scope determining device 19 or the like which stores information on the type or the like of the scope 2.

An operating portion (not shown) arranged on the proximal-end side of the scope 2 comprises: a filter selection switch 16, which generates an instructing signal issued by switching the infrared/visible switching filter 9, provided at the position for easy pressing operation for a user; a release switch 17 which generates an instructing signal that causes an execution of the recording operation by an image recording device such as the digital filing device 5 or photographing device 6; and the like.

The processor 3 comprises: two pre-processing circuits 20 for an A-channel and B-channel; two A/D converting circuits 21 for the A-channel and B-channel; two color balance correcting circuits 22 for the A-channel and B-channel; a multiplexer 23; three simultaneity memories 24r, 24g, and 24b; an image processing circuit 25; a color-tone adjusting circuit 26; three D/A converting circuits 27r, 27g, and 27b; an encoding circuit 28; a dimmer circuit 29; an exposure period control circuit 30; and a CPU 31 which integrally controls the circuits in the processor 3.

A front panel (not shown) of the processor 3 comprises various switches operated by the user, e.g., a color balance setting switch 32, an image processing setting switch 33, and a color-tone setting switch 34.

The CPU 31 detects states of the color balance setting switch 32, the image processing setting switch 33, and the color-tone setting switch 34.

Further, the CPU 31 detects states of the filter selection switch 16 and the release switch 17 of the scope 2, and reads the information stored in the scope determining device 19.

Furthermore, the CPU 31 outputs an image recording instructing signal as a control signal for instructing the operation for recording the image to the digital filing device 5 or photographing device 6, and a filter switching instructing signal as a control signal for instructing the operation for switching the infrared/visible switching filter 9 to the light source device 7.

In addition to the indication in FIG. 1, the CPU 31 outputs predetermined control signals to units of the processor 3.

Referring to FIG. 1, the lamp 8 of the light source device 7 radiates light having the wavelength including a visible area and a near infrared area. The light irradiated from the lamp 8 passes through the infrared/visible switching filter 9, the illuminating light aperture stop 13, and the RGB-rotating filter 11, and is incident on the light guide fiber 14 of the scope 2.

Figure 2:
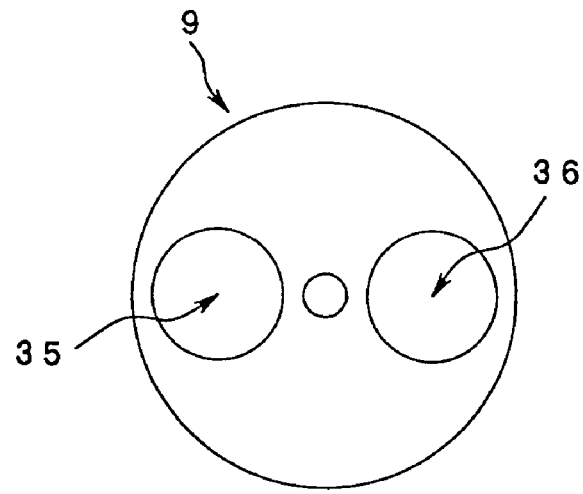
FIG. 2 is a diagram showing the structure of an infrared/visible switch filter.
Figure 3:
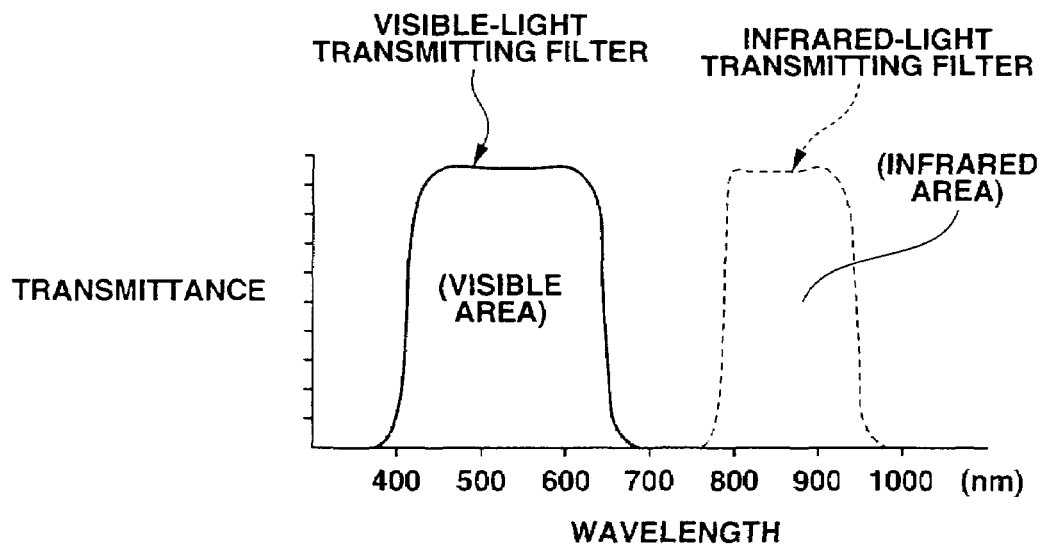
FIG. 3 is a diagram showing the optical transparency of a visible-light transmitting filter and an infrared-light transmitting filter.

Referring to FIG. 2, the infrared/visible switching filter 9 comprises two filters including a visible light transmitting filter 35 through which the visible light is transmitted; and an infrared light transmitting filter 36 through which the infrared light is transmitted. Driving force of the motor 10 rotates the infrared/visible switching filter 9, thereby switching the filter inserted in the optical path. Referring to FIG. 3, through the visible light transmitting filter 35, the light having the wavelength in the visible area is transmitted. Similarly, referring to FIG. 3, through the infrared light transmitting filter 36, the light having the wavelength in the near infrared area is transmitted.

An illuminating light aperture stop 13 limits the light amount of luminous flux outputted from the light source device 7 in accordance with a dimmer signal outputted from the dimmer circuit 29 in the processor 3 so as to prevent the saturation in the image picked-up by the image pick-up device 15.

Figure 4:
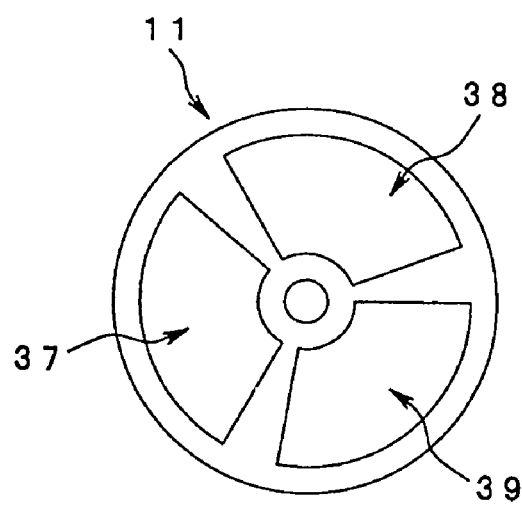
FIG. 4 is a diagram showing the structure of an RGB rotating filter.

Referring to FIG. 4, the RGB rotating filter 11 comprises three filters of an R-filter 37, a G-filter 38, and a B-filter 39. The R-filter 37, the G-filter 38, and the B-filter 39 are rotated by the motor 12 and, thus, the light having different wavelength bands are transmitted through the R-filter 37, the G-filter 38, and the B-filter 39.

Figure 5:
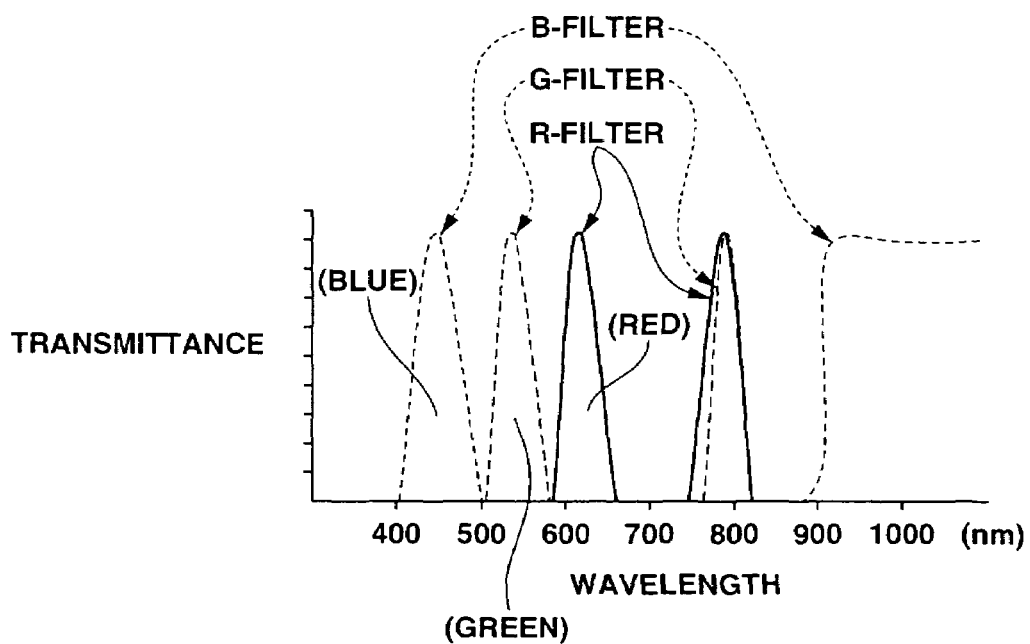
FIG. 5 is a diagram showing the optical transparency of an R-filter, a G-filter, and a B-filter.

Referring to FIG. 5, the R-filter 37, the G-filter, and the B-filter transmit respectively the red, green, and blue luminous fluxes when the wavelengths are in the visible area. That is, when the visible light transmitting filter 35 is inserted in the optical path, the red, green, and blue luminous fluxes are transmitted through the RGB rotating filter 11.

Further, referring to FIG. 5, through the R-filter 37, the G-filter 38, and the B-filter 39, not only the light having the wavelength in the visible area but also light having the wavelength in the infrared area is transmitted. Therefore, when the infrared light transmitting filter 36 is inserted in the optical path, the luminous fluxes having the wavelengths of 805 nm±15 nm, 805 nm±15 nm, and 930 nm±20 nm are transmitted.

The luminous flux incident on the light guide fiber 14 are outputted from the distal end of the scope 2, and are irradiated to the object such as the digestive tract. The image pick-up device 15 arranged to the distal portion of the scope 2 receives the light which is scattered and reflected by the object. Further, the image pick-up device 15 is controlled and driven simultaneously with the rotation of the RGB rotating filter 11. Thus, the image signals corresponding to the illuminating light through the R-filter 37, the G-filter 38, and the B-filter 39 are sequentially outputted to the processor 3.

Figure 6:
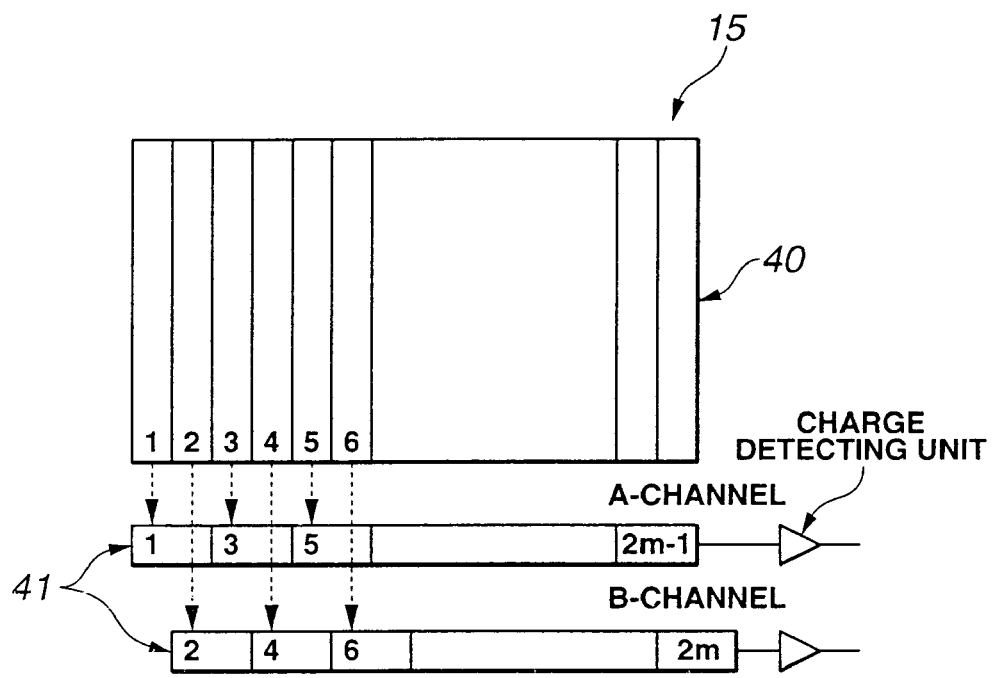
FIG. 6 is a diagram showing the schematic structure of an image pick-up device.

Referring to FIG. 6, charges stored in the image pick-up device 15 are vertically transferred downward from a light receiving area 40. Then, the charges of a pixel in an odd column and the charges of a pixel in an even column are horizontally transferred via individual routes (horizontal transfer register 41), the charges are converted into a voltage by a charge detecting unit, and they are outputted to the processor 3.

In the description according to the embodiment, for the purpose of a brief description, the A-channel denotes a route through which the image signal passes corresponding to the pixel in the odd column of the image pick-up device 15, and the B-channel denotes a route through which the image signal passes corresponding to the pixel in the even column.

Therefore, the image signals in the A-channel and B-channel are outputted to the processor 3 from the image pick-up device 15.

Figure 7:
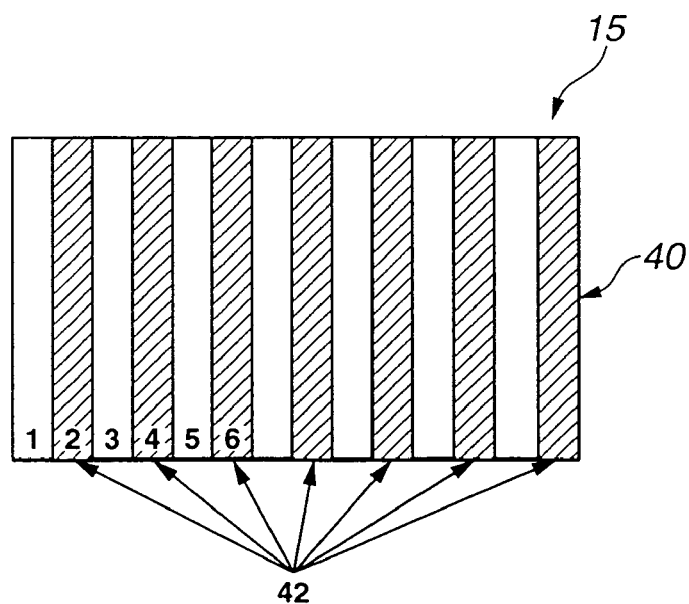
FIG. 7 is a diagram showing the arrangement of an infrared-light cut filter.

Referring to FIG. 7, an infrared-light cut filter 42 is arranged to the even columns (portion indicated by diagonal lines in FIG. 7) with the width corresponding to the image column of the image pick-up device 15.

Figure 8:
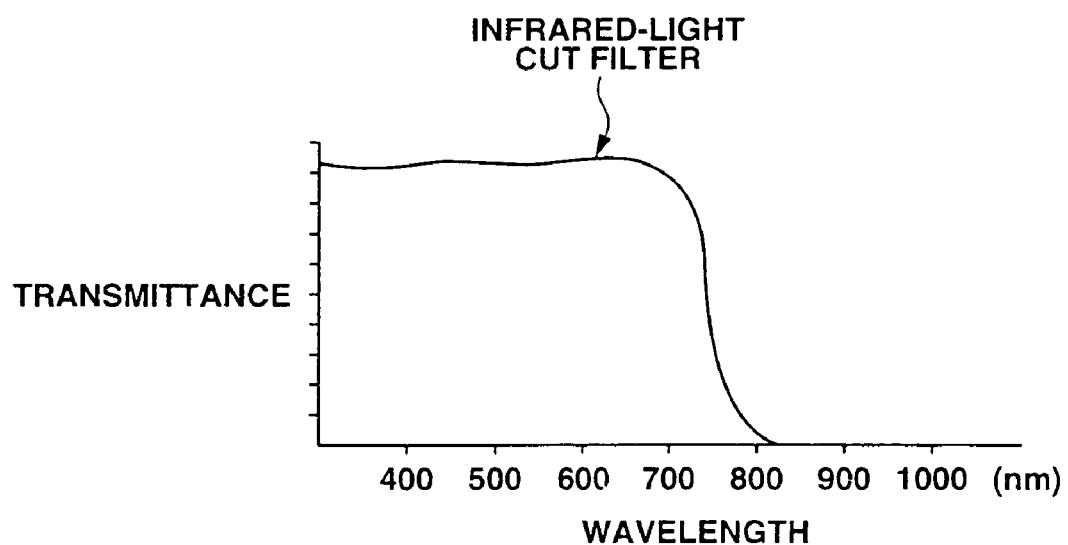
FIG. 8 is a diagram showing the optical transparency of the infrared-light cut filter.

Referring to FIG. 8, the infrared-light cut filter 42 attenuates the light having the wavelength constituting the infrared-light component of approximately 805 nm, and transmits most of the light in the visible area. Therefore, in the light receiving area 40 of the image pick-up device 15, the image signal (refer to FIG. 6) of the A-channel read from the pixel in the odd column, where the infrared-light cut filter 42 is not arranged, includes the infrared-light component. On the other hand, the light receiving area 40 of the image pick-up device 15, the image signal (refer to FIG. 6) of the B-channel read from the pixel in the even column, where the infrared-light cut filter 42 is arranged, does not include the infrared-light component.

The image pick-up device 15 incorporates an electric shutter (not shown), as means for adjusting the accumulation period of charges. The electric shutter adjusts the exposure period of the image which is obtained by adjusting the time from the output operation to the reading operation of charges.

The image signals inputted to the processor 3 through the two channels constituting the A- and B-channels are inputted to the two pre-processing circuits 20 arranged individually, are subjected to the signal processing such as CDS (Correlative Double Sampling), and then are individually outputted.

The two-channel image signals outputted respectively from the pre-processing circuits 20 of the A- and B-channels are converted into digital signals from analog signals by the two A/D converting circuits 21 that are individually arranged. Then, the signals are outputted to the two color balance correcting circuits 22 that are individually arranged.

Figure 9:
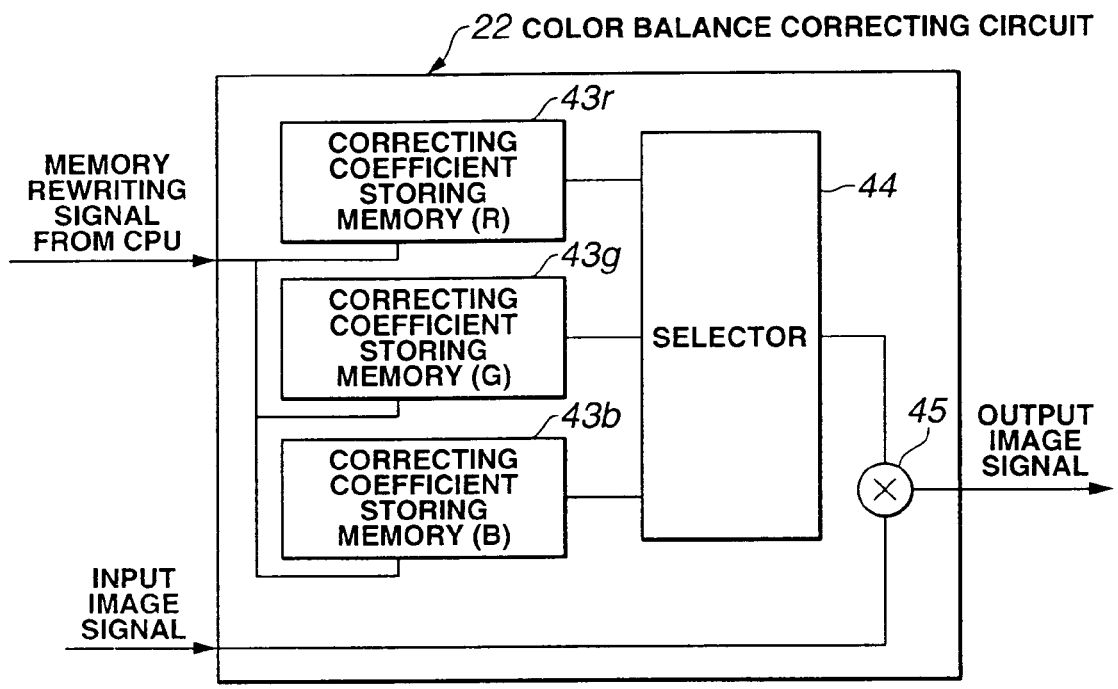
FIG. 9 is a block diagram showing the structure of a color balance correcting circuit.

The two color balance correcting circuits 22 have the same structure. Referring to FIG. 9, each of the color balance correcting circuits 22 comprises: color balance correcting coefficient storing memories (for R, G, and B) 43r, 43g, and 43b; a selector 44 which selects the color balance correcting coefficient; and a multiplier 45.

The color balance correcting coefficients calculated by the CPU 31 are written to the color balance correcting coefficient storing memories 43r, 43g, and 43b.

The color balance correcting coefficient storing memories 43r, 43g, and 43b of the color balance correcting circuit 22 of the A-channel store any of the color balance correcting coefficients for the infrared image or visible image, in accordance with the switching of the infrared/visible switching filter 9. The color balance correcting coefficient for the visible image is always written to the color balance correcting coefficient storing memories 43r, 43g, and 43b of the color balance correcting circuit 22 of the B-channel.

The selector 44 selects the color balance correcting coefficient storing memory 43r when the R-filter 37 (refer to FIG. 4) of the RGB rotating filter 11 is inserted in the optical path. Further, the selector 44 selects the color balance correcting coefficient storing memory 43g when the G-filter 38 (refer to FIG. 4) of the RGB rotating filter 11 is inserted in the optical path. Furthermore, the selector 44 selects the color balance correcting coefficient storing memory 43b when the B-filter 39 (refer to FIG. 4) of the RGB rotating filter 11 is inserted in the optical path.

The multiplier 45 multiplies the input image signal by the color balance correcting coefficient selected by the selector 44, and outputs.

The image signals outputted from each of the color balance correcting circuits 22 are outputted to the multiplexer 23. In the normal case (observation using the visible light), the multiplexer 23 alternately extracts the image signals of the A- and B-channels and returns the extracted signals to the pixel arrangement on the light receiving area 40 in the image pick-up device 15, and the images while the R-filter 37, G-filter 38, and B-filter 39 are inserted in the optical path are distributed and stored in the simultaneity memories 24r, 24g, and 24b.

In the observation using the infrared light, the multiplexer 23 always reads the output signal from the color balance correcting circuit 22 of the A-channel, and interpolates the image signal of which pixel positions correspond to the ones in the even column on the light receiving area 40 of the image pick-up device 15 by reading, twice, the image signal of the pixel corresponding to the same pixel in the A-channel. Further, the interpolated signal is outputted to the simultaneity memories 24r, 24g, and 24b, and the simultaneity memories 24r, 24g, and 24b store the input image signal.

The image signals stored in the simultaneity memories 24r, 24g, and 24b are subjected to the simultaneity processing of the image signals (so-called field-sequential image signals) when the R-filter 37, G-filter 38, and B-filter 39 are inserted in the optical path.

The output signal from the color balance correcting circuit 22 of the A-channel is inputted to the dimmer circuit 29. The dimmer circuit 29 forms the dimmer signal to keep the brightness of the obtained image constant depending on the size of the input image signal. The dimmer signal adjusts the light amount outputted from the light source device 7 by controlling the illuminating light aperture stop 13 in the light source device 7. The dimmer circuit 29 is controlled by a predetermined control signal from the CPU 31.

The exposure period control circuit 30 receives the output signal from the color balance correcting circuit 22 of the B-channel. The exposure period control circuit 30 outputs an electric shutter control signal for controlling an electric shutter exposure period of the image pick-up device 15 so as to keep the brightness of the obtained image constant according to the size of the input image signal.

That is, the exposure period control circuit 30 controls the exposure period by a predetermined control signal from the CPU 31 such that the exposure period is maximum.

Figure 10:
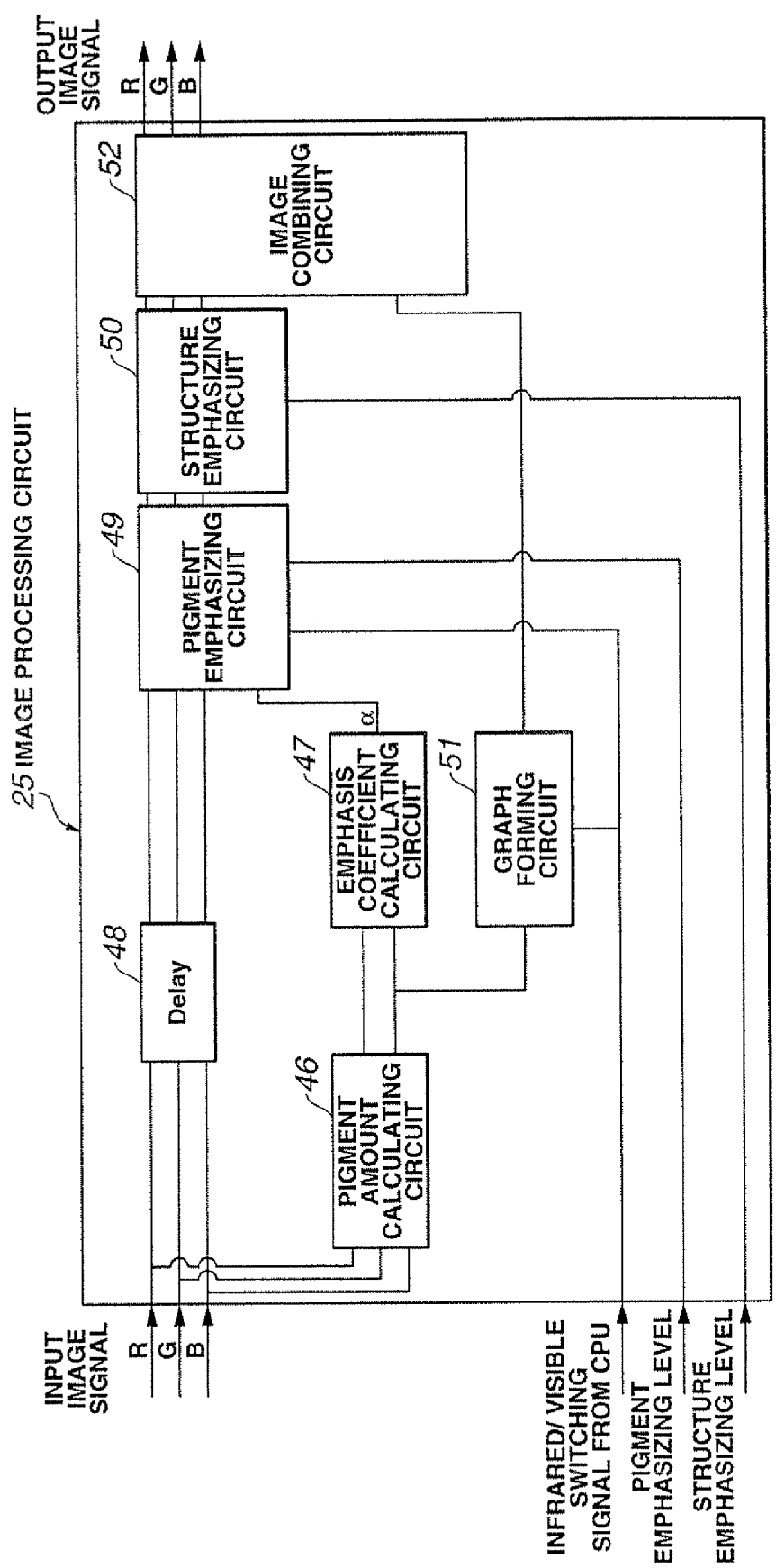
FIG. 10 is a block diagram showing the structure of an image processing circuit.

Referring to FIG. 10, the image processing circuit 25 comprises: a pigment amount calculating circuit 46; an emphasis coefficient calculating circuit 47; a delay circuit 48 which adjusts the timing of the image signal; a pigment emphasizing circuit 49 which emphasizes the color; a structure emphasizing circuit 50; a graph forming circuit 51 which forms the graph of the pigment amount that is displayed on the monitor 4; and an image combining circuit 52.

The image processing circuit 25 receives the image signals made simultaneous by the simultaneity memories 24r, 24g, and 24b.

According to the embodiment, conveniently, signals R, G, and B denote three signals forming the image signals at the respective positions of the route from the simultaneity memories 24r, 24g, and 24b to the monitor 4. In this case, the signals R, G, and B of the visible image denote signals of a red component, a green component, and a blue component. In the meantime, conveniently, the signals R, G, and B in the infrared image denote the signals transferred by cables for transferring the signals R, G, and B in the visible image. Again, conveniently, the signals R, G, and B in the field-sequential image denote the signals R, G, and B.

The image processing circuit 25 calculates the pigment amount based on the input image signal by the pigment amount calculating circuit 46. The pigment amount calculating circuit 46 calculates the pigment amount (hereinafter, referred to as hemoglobin amount) indicating the hemoglobin amount for the visible image in accordance with an infrared/visible switching signal from the CPU 31. Further, the image processing circuit 25 calculates the pigment amount (hereinafter, referred to as ICG amount) indicating the Indocyanine Green (ICG) as the pigment for absorbing the infrared rays for the infrared image.

Figure 11:
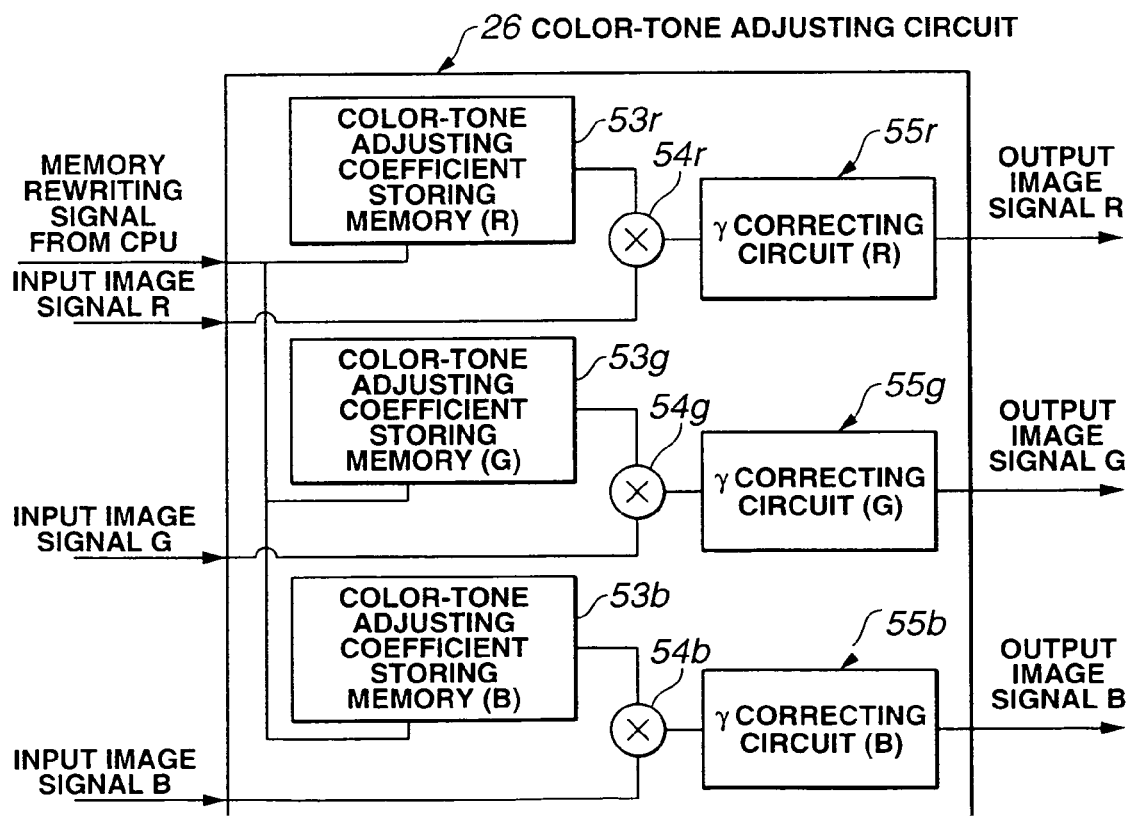
FIG. 11 is a block diagram showing the structure of a color-tone adjusting circuit.

Referring to FIG. 11, the color-tone adjusting circuit 26 comprises: three color-tone adjusting coefficient storing memories 53r, 53g, and 53b, as non-volatile memories, for storing color-tone adjusting coefficients R, G, and B; three multipliers 54r, 54g, and 54b; and three gamma (γ) correcting circuits 55r, 55g, and 55b.

The color-tone adjusting circuit 26 receives an output signal from the image processing circuit 25. The CPU 31 writes the color-tone adjusting coefficients R, G, and B corresponding to the signals R, G, and B of the input image signal from the color-tone adjusting circuit 26 to the color-tone adjusting coefficient storing memories 53r, 53g, and 53b.

The multipliers 54r, 54g, and 54b multiply the input image signals (signals R, G, and B) from the image processing circuit 25 by the color-tone adjusting coefficients R, G, and B stored in the color-tone adjusting coefficient storing memories 53r, 53g, and 53b. Then, the multiplied signals are converted into the color tones set by the user.

The signals outputted from the multipliers 54r, 54g, and 54b are inputted to the gamma correcting circuits 55r, 55g, and 55b, and are subjected to predetermined gamma correcting processing, that is, conversion processing for correcting the gamma characteristics of the monitor 4, thus to be outputted as the output image signals R, G, and B.

The image signals (signals R, G, and B) outputted from the color-tone adjusting circuit 26 are inputted to the D/A converting circuits 27r, 27g, and 27b (refer to FIG. 1). After the input signals are converted into the analog signals, the converted signals are outputted to the monitor 4. In response to the output signal, the monitor 4 displays the image of the object.

Figure 12:
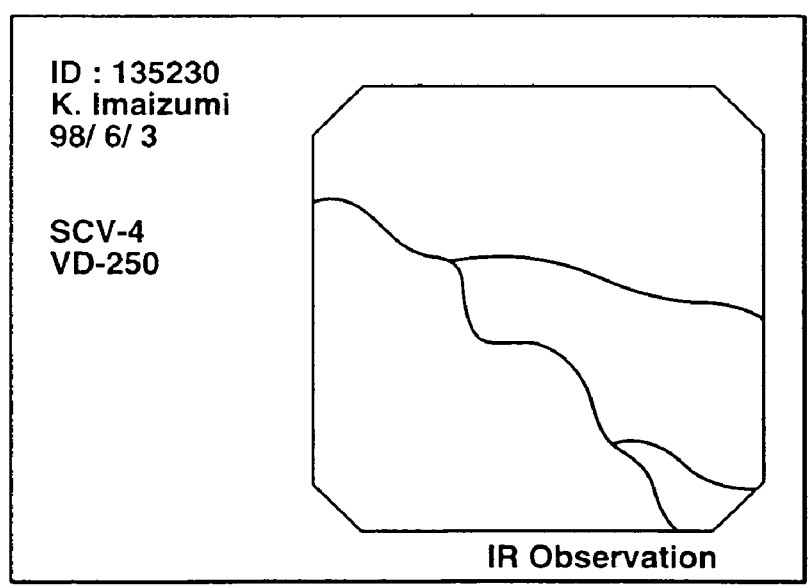
FIG. 12 is a diagram showing an example of a display screen.

FIG. 12 shows an example of a display screen of the monitor 4 upon displaying the infrared image.

Referring to FIG. 12, the infrared image is displayed in the octagonal portion on the right side of the screen. Near the bottom edge portion of the image, a characteristic string "IR Observation" indicating that the image is currently displayed is the infrared image is displayed. At the area on the left side of the screen, various pieces of information related to the image that is currently displayed is displayed by using a character.

The image signals (signals R, G, and B outputted form the color-tone adjusting circuit 26 are outputted to the encoding circuit 28. In response to the output signal, the encoding circuit 28 transmits the image signal which has been subjected to the predetermined encoding processing to the digital filing device 5 or photographing device 6. Then, the image signal or image in the devices is recorded in accordance with an image recording instructing signal from the CPU 31.

The CPU 31 has therein a non-volatile memory area for storing set values of various coefficients which are used by the color balance correcting circuit 22, image processing circuit 25, and image processing circuit 25.

Here, a brief description is given of the internal memory structure of the CPU 31. FIG. 13 shows a part of an internal memory map of the CPU 31.

The color balance correcting coefficient is a predetermined set value that is stored by the user by setting the color balance in accordance with the sequence, which will be described later.

The pigment emphasizing level, structure emphasizing level, and color-tone adjusting level indicate the set values which are updated by changing the set values (set levels) by operating the front panel by the user.

The color-tone adjusting coefficient is the set value that is previously stored in the CPU 31, and is further the set value that is outputted to the color-tone adjusting circuit 26 in accordance with the set level determined by changing the color-tone adjusting level by the user.

As mentioned above, the internal memory of the CPU 31 functions as means storing the color balance correcting amount, color-tone adjusting value, and image processing set value.

Further, the CPU 31 outputs an instructing signal that sets the filter switching or various set values during the vertical fly-back period so as to prevent the disturbance of the image.

In addition, the CPU 31 determines by reading the information stored in the scope determining device 19 incorporated in the scope 2 whether or not the connected scope 2 is an infrared scope. The infrared scope here has the image pick-up device 15 shown in FIG. 7. That is, the type of infrared scope includes the infrared cut filters 42 that are arranged to parts of the front side of the light receiving area 40 of the image pick-up device 15.

A scope that is not suitable to the infrared light has an infrared cut filter onto the entire light-receiving surface of the image pick-up device, so that the scope is not suitable to the infrared observation.

In the following description, an observing apparatus sometimes is referring to a series of the light source device 7, and the monitor 4 and the scope 2 comprising an image pick-up device including the image pick-up device 15.

Hereinbelow, a description is given of the operation of the endoscope apparatus 1 forming a part of the infrared observing system with the above-mentioned structure according to the embodiment.

The lamp 8 of the light source device 7 irradiates light having the wavelength area including the visible area and the infrared area. The light irradiated from the lamp 8 sequentially passes through the infrared/visible switching filter 9, illuminating light aperture stop 13, and RGB rotating filter 11, and is incident on the light guide fiber 14 of the scope 2.

The infrared/visible switching filter 9 is rotated by driving force of the motor 10 that is driven in accordance with the filter switching instructing signal from the CPU 31. Thus, one of the visible light transmitting filter 35 and the infrared light transmitting filter 36 is inserted and is held onto the optical path.

The illuminating light aperture stop 13 limits the light amount of the luminous flux outputted form the light source device 7 in accordance with the dimmer signal outputted from the dimmer circuit 29 of the processor 3 so as to prevent the saturation of the image picked-up by the image pick-up device 15.

The RGB rotating filter 11 is rotated and driven by the motor 12 that is driven in accordance with the instructing signal from the CPU 31. Thus, the read, green, and blue luminous fluxes sequentially pass through the visible light transmitting filter 35, upon inserting the visible light transmitting filter 35 into the optical path. In place of the read, green, and blue luminous fluxes, the luminous fluxes of the wavelength of 805 nm±15 nm, 805 nm±15 nm, and 930 nm±20 nm are transmitted and are outputted from the light source device 7.

The luminous flux incident on the light guide fiber 14 of the scope 2 are outputted from the distal end of the scope 2 and are irradiated to the object such as the digestive tract. The image pick-up device 15 arranged to the distal portion of the scope 2 receives the light which is scattered and is reflected by the object. The image pick-up device 15 is driving-controlled simultaneously with the rotation of the RGB rotating filter 11 and thus the image signals corresponding to the illuminated light through the R-filter 37, G-filter 38, and B-filter 39 are sequentially outputted to the processor 3.

The charges stored in the image pick-up device 15 are vertically transferred down from the light receiving area 40.

Then, the charges are horizontally transferred by the two channels (horizontal transfer registers 41) of the A- and B-channels, that is, the charges of the pixel in the odd column are horizontally transferred through the A-channel and the charges of the pixel in the even column are horizontally transferred through the B-channel. After that, the charges are converted into the voltage by a charge detecting unit and are outputted to the processor 3 (refer to FIG. 6).

As mentioned above, the infrared-light component is included in the image signal (refer to FIG. 6) of the A-channel read from the pixel in the odd column which does not include the infrared-light cut filter 42 of the light receiving area 40 in the image pick-up device 15. The infrared-light component is not included in the image signal (refer to FIG. 6) of the B-channel read from the pixel in the even column which includes the infrared-light cut filter 42. The image pick-up device 15 adjusts the time from the sweeping of charges to the reading thereof by the electric shutter to obtain an image. Then, the image pick-up device 15 adjusts the exposure period of the obtained image.

The image signals through the two channels of the A- and B-channels inputted to the processor 3 are first inputted to the two pre-processing circuits 20. The pre-processing circuits 20 perform the signal processing such as CDS (correlative double sampling), and extract the image signals. The two image signals outputted from the pre-processing circuits 20 through the A- and B-channels are converted into the digital signals from the analog signals by the two A/D converting circuits 21. Then, the signals are outputted to the two color balance correcting circuits 22.

The selector 44 in the color balance correcting circuit 22 selects the color balance correcting coefficient storing memory 43r at the timing for inserting in the optical path the R-filter 37 (refer to FIG. 4) of the RGB rotating filter 11. Further, the selector 44 selects the color balance correcting coefficient storing memory 43g at the timing for inserting in the optical path the G-filter 38 (refer to FIG. 4) of the RGB rotating filter 11. Furthermore, the selector 44 selects the color balance correcting coefficient storing memory 43b at the timing for inserting the B-filter 39 (refer to FIG. 4) of the RGB rotating filter 11 in the optical path.

The multiplier 45 multiplies and outputs the input image signal to the color balance correcting coefficient selected by the selector 44.

The color balance correcting coefficients calculated by the CPU 31 are written to the color balance correcting coefficient storing memories 43r, 43g, and 43b. The color balance correcting coefficient storing memories 43r, 43g, and 43b of the color balance correcting circuit 22 of the A-channel store any of the color balance correcting coefficients for the infrared image or visible image, in synchronizing with the switching of the infrared/visible switching filter 9. The color balance correcting coefficient for the visible image is always written to the color balance correcting coefficient storing memories 43r, 43g, and 43b of the color balance correcting circuit 22 of the B-channel.

The image signals outputted from the color balance correcting circuits 22 are outputted to the multiplexer 23. In the normal case (observation using the visible light), the multiplexer 23 alternately extracts the image signals of the A- and B-channels and returns the extracted signals to the pixel arrangement on the light receiving area 40 in the image pick-up device 15, and the images upon inserting the R-filter 37, G-filter 38, and B-filter 39 in the optical path are distributed and are stored in the simultaneity memories 24r, 24g, and 24b.

In the observation using the infrared light, the multiplexer 23 regularly reads the output signal from the color balance correcting circuit 22 of the A-channel, and interpolates the image signal of which pixel positions correspond to the ones in the even column on the light receiving area 40 of the image pick-up device 15 by reading twice the image signal of the pixel corresponding to the same pixel in the A-channel and, the interpolated signal is outputted to the simultaneity memories 24r, 24g, and 24b, and the simultaneity memories 24r, 24g, and 24b store the input image signals. The image signals stored in the simultaneity memories 24r, 24g, and 24b are subjected to the simultaneity processing of the field-sequential image by simultaneously reading the image signals.

The output signal from the color balance correcting circuit 22 of the A-channel is inputted to the dimmer circuit 29. The dimmer circuit 29 receives control signals from the CPU 31 and creates the dimmer signal for keeping the brightness of the obtained image substantially constant on the basis of the size of the input signal from the A-channel. The created dimmer signal is transmitted to the light source device 7 and then controls the illuminating light aperture stop 13, thus to adjust the light amount outputted from the light source device 7.

The exposure period control circuit 30 receives the output signal from the color balance correcting circuit 22 of the B-channel. The exposure period control circuit 30 outputs an electric shutter control signal for controlling an electric shutter exposure period of the image pick-up device 15 so as to keep the brightness of the obtained image substantially constant on the basis of the size of the signal from the B-channel. That is, the exposure period control circuit 30 controls the exposure period by a predetermined control signal from the CPU 31 such that the exposure period becomes maximum.

As mentioned above, the image signals made simultaneous by the simultaneity memories 24r, 24g, and 24b are inputted to the image processing circuit 25 and are subjected to the predetermined image processing.

The image processing circuit 25 first calculates the pigment amount based on the input image signal by the pigment amount calculating circuit 46. The pigment amount calculating circuit 46 calculates every pixel the pigment amount indicating the Indocyanine Green amount (hereinafter, abbreviated to the ICG amount) for the infrared image in accordance with the infrared/visible switching signal from the CPU 31.

Hereinbelow, a detailed description is given of the calculation of the ICG amount every pixel by using the pigment amount calculating circuit 46.

That is, the formula for obtaining the ICG amount IIcg is as follows.

$$IIcg = \log(B/R)$$

The pigment amount calculating circuit 46 outputs an average pigment amount as the average of the pigments amount of one frame of the image in addition to the pigment amount (ICG amount) every pixel.

The pigment amount and the average pigment amount calculated by the pigment amount calculating circuit 46 are inputted to the emphasis coefficient calculating circuit 47 and, further, the emphasizing coefficient is calculated every pixel based on the difference between the pigment amount and the average pigment amount. In the case of the infrared observation (calculation of IIcg), an emphasizing coefficient $\alpha$ is expressed as follows.

$$\alpha = IIcg - Ave(IIcg)$$

Here, reference symbol Ave (IIcg) denotes the average of one frame of the image of the IIcg. The image having the deviated distribution is effectively emphasized by obtaining the difference between the pigment amount of the pixel and the average of one frame.

The pigment emphasizing circuit 49 performs the color emphasis on the basis of the pigment amount every pixel, based on the emphasizing coefficient $\alpha$, the image signal whose timing is adjusted by the delay circuit 48, and the pigment emphasizing level designated by the CPU 31. Relational formulae between the input signal and the output signal of the pigment emphasizing circuit 49 are expressed as follows.

$$Rout = Rin \times \exp(h \times kR \times \alpha)$$

$$Gout = Gin \times \exp(h \times kG \times \alpha)$$

$$Bout = Bin \times \exp(h \times kB \times \alpha)$$

Here, reference symbols Rin, Gin, and Bin denote input image signals of the signals R, G, and B, respectively. Reference symbols Rout, Gout, and Bout denote output image signals of the signals R, G, and B, respectively. Reference symbols kR, kG, and kB denote coefficients which are determined based on absorbing ratios every color of the pigments as the target. Reference symbol h denotes a coefficient indicating the emphasizing degree, and is determined based on the pigment emphasizing level that is set by the CPU 31. The color emphasis forms the image having the seemingly increased ICG amount (IIcg) upon the emphasis based on the ICG amount (IIcg). The pigment emphasizing circuit 49 switches and calculates the values kR, kG, and kB for infrared light or the ones for visible light in accordance with the infrared/visible switching signal from the CPU 31.

Reference symbol $\alpha$ denotes the emphasizing coefficient as the difference between the pigment amount and the average pigment amount which are calculated by the emphasis coefficient calculating circuit 47.

The image signal outputted from the pigment emphasizing circuit 49 is emphasized by a spatial filter so as to emphasize the fine pattern on the mucosa of the living body by the structure emphasizing circuit 50. The emphasizing degree of the structure by the structure emphasizing circuit 50 is determined based on the structure emphasizing level outputted from the CPU 31.

The output signal from the image processing circuit 25 is inputted to the color-tone adjusting circuit 26 (refer to FIG. 11). The CPU 31 writes the corresponding color-tone adjusting coefficients R, G, and B to the color-tone adjusting coefficient storing memories 53r, 53g, and 53b.

Next, the multipliers 54r, 54g, and 54b multiply the color-tone adjusting coefficients R, G, and B and the input image signals, and convert the multiplied signals into the color tones set by the user.

The output signals from the multipliers 54r, 54g, and 54b are respectively subjected to predetermined gamma correcting processing (converting processing for correcting the gamma characteristics of the monitor 4) by the gamma correcting circuits 55r, 55g, and 55b (refer to FIG. 11) The output signals (digital signals) from the color-tone adjusting circuit 26 are converted into the analog signals by the D/A converting circuits 27r, 27g, and 27b (refer to FIG. 1). Then, the analog signal is outputted to the monitor 4. In accordance therewith, the monitor 4 displays the image of the object.

The output signal from the color-tone adjusting circuit 26 is outputted to the encoding circuit 28. In accordance therewith, the encoding circuit 28 performs predetermined encoding processing. The above-generated digital image signal is outputted to the digital filing device 5 or photographing device 6, and the corresponding device records the image signal or image in accordance with the image recording instructing signal from the CPU 31.

The infrared image shown in FIG. 12 is displayed on the monitor 4 upon the infrared light transmitting filter 36 being inserted in the optical path. Referring to FIG. 12, the infrared image is displayed in the octagonal portion on the right side of the screen. As mentioned above, the character string "IR Observation" is displayed at the predetermined position on the display screen, indicating that the display image is the infrared image.

Hereinbelow, a description is given of the operation upon pressing the filter selection switch 16 of the scope 2 by the user with reference to the flowchart of FIG. 14.

The user presses the filter selection switch 16, then, the filter switching instructing signal is generated, and the instructing signal is transmitted to the CPU 31. In accordance therewith, the CPU 31 executes the flowchart shown in FIG. 14, that is, the processing sequence of the filter switching processing.

Figure 14:
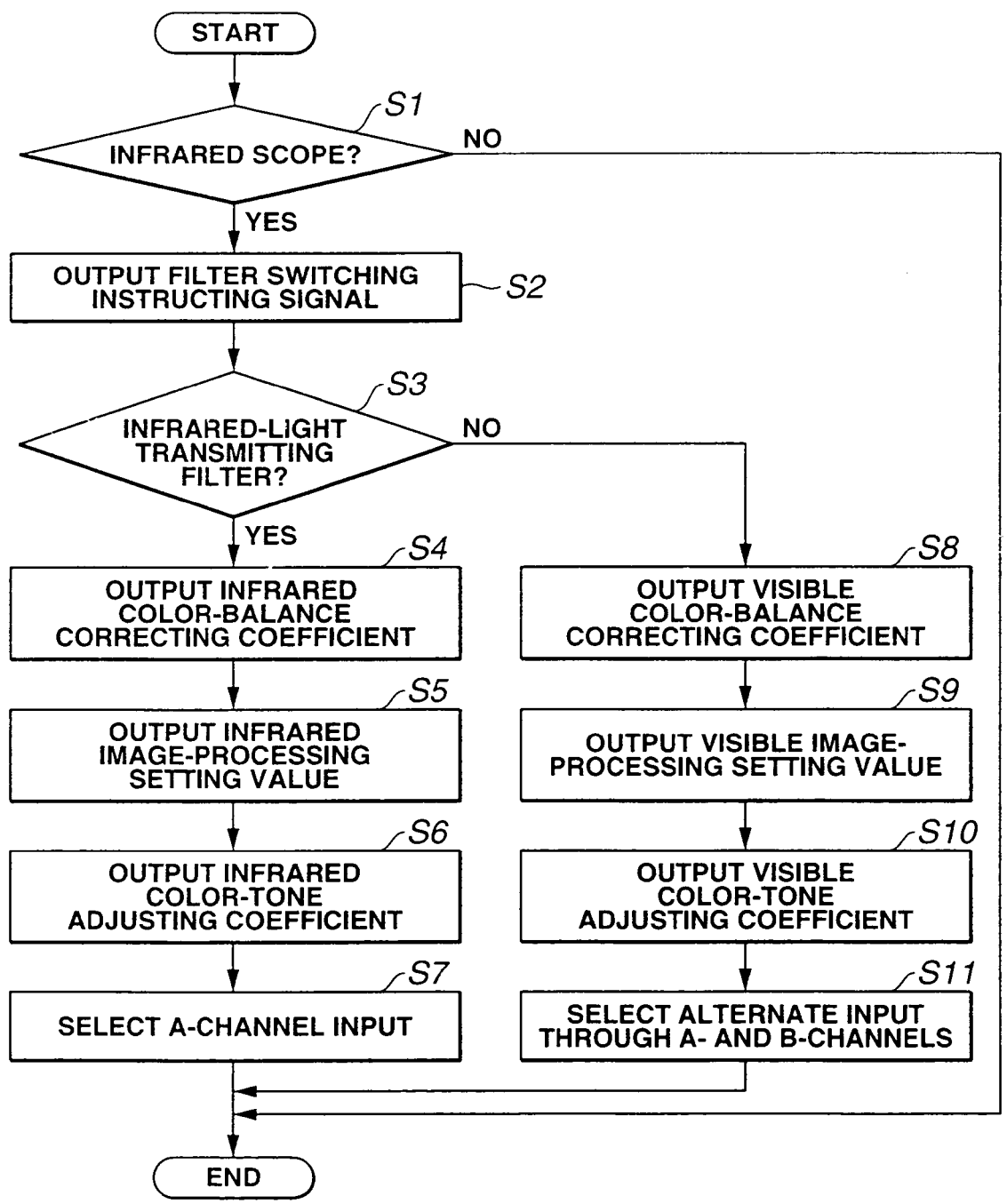
FIG. 14 is a flowchart for explaining the flow of filter switching processing.

In step S1 in FIG. 14, the CPU 31 determines whether or not the connected scope 2 is the infrared scope that does not correspond to the infrared image. In this case, the CPU 31 determines it by reading the information of the scope determining device 19 incorporated in the scope 2. When the CPU 31 determines that the connected scope 2 is not the infrared scope, the CPU 31 does not execute anything and ends the processing.

When the CPU 31 determines that the connected scope 2 is the infrared scope, the processing sequence shifts to step S2.

In step S2, the CPU 31 outputs the filter switching instructing signal to the light source device 7. In response to the output, the motor 10 of the light source device 7 is driven. Thus, the infrared/visible switching filter 9 is operated and, when the visible light transmitting filter 35 is currently in the optical path, the infrared/visible switching filter 9 switches the filter to the infrared light transmitting filter 36. When the infrared light transmitting filter 36 is currently in the optical path, the infrared/visible switching filter 9 switches the filter to the visible light transmitting filter 35. After that, the processing sequence advances to step S3.

In step S3, the CPU 31 confirms whether the filter in the optical path is the infrared light transmitting filter 36 or the visible light transmitting filter 35. When the CPU 31 confirms that the infrared light transmitting filter 36 is inserted in the optical path, the processing sequence advances to step S4. When the CPU 31 confirms that the visible light transmitting filter 35 is inserted in the optical path, the processing sequence advances to step S8.

It is determined in step S3 that the infrared light transmitting filter 36 is inserted in the optical path and the processing sequence advances to step S4. Then, in step S4, the color balance correcting coefficient for infrared light is written to the color balance correcting coefficient storing memory 43 of the color balance correcting circuit 22 of the A-channel. After that, the processing sequence shifts to step S5.

In step S5, the image emphasizing level for infrared light (pigment emphasizing level and structure emphasizing level) and the infrared/visible switching signal are transmitted to the image processing circuit 25. Thereafter, the processing sequence shifts to step S6.

In step S6, the color-tone adjusting coefficient for infrared light is written to the color-tone adjusting coefficient storing memories 53r, 35q, and 53b. Then, the processing sequence shifts to step S7.

In step S7, the multiplexer 23 all the time selects the signal of the A-channel. Then, a series of processing ends.

Since the signal of the A-channel is a signal of the pixel for transmitting the infrared light, the infrared image of the object is preferably picked up. However, the signals of the same pixel are aligned in the lateral direction, by two pixels, and therefore the resolution in the lateral direction deteriorates as compared with the normal image (image of the visible light).

It is confirmed in step S3 that the visible light transmitting filter 35 is inserted in the optical path and then the processing sequence shifts to step S8. In step S8, the color balance correcting coefficient for visible light is written to the color balance correcting coefficient storing memory 43 of the A-channel. After that, the processing sequence shifts to step S9.

In step S9, the image emphasizing level for the visible light and the infrared/visible switching signal are transmitted to the image processing circuit 25. Then, the processing sequence shifts to step S10.

In step S10, the color-tone adjusting coefficient for visible light is written to the color-tone adjusting coefficient storing memories 53r, 53q, and 53b. Then, the processing sequence shifts to step S11.

In step S11, the multiplexer 23 sets every pixel so as to input, alternately, the signal of the A-channel and the signal of the B-channel, and the series of processing ends.

After the above filter switching processing, the CPU 31 switches the visible light transmitting filter 35 and the infrared light transmitting filter 36. In accordance therewith, various setting values are read from the internal memory and are switched. Therefore, the user observes the preferable image without troublesome operation.

The switching of the multiplexer 23 enables the acquisition of the high-resolution image using the entire pixels of the image pick-up device 15 upon the visible-light observation. Upon infrared-light observation, the bright infrared image is obtained by using the pixel having no arrangement of the infrared-light cut filter 42.

Hereinbelow, a description is given of the operation upon setting the color balance with reference to the flowchart of FIG. 15.

Upon setting the color balance, the user picks up the image of the substance having the reference color and presses the color balance setting switch 32 arranged to the front panel of the processor 3. The substance having the reference color in this case has a prescribed reflectance ranged from the visible light to the near infrared wavelength of 1,000 nm, and constitutes the color reference.

As mentioned above, the color balance setting switch 32 is pressed and then a color balance setting requesting signal is transmitted to the CPU 31. The CPU 31 receives the color balance setting requesting signal and executes the flowchart shown in FIG. 15, that is, the processing sequence of the color balance setting processing.

Figure 15:
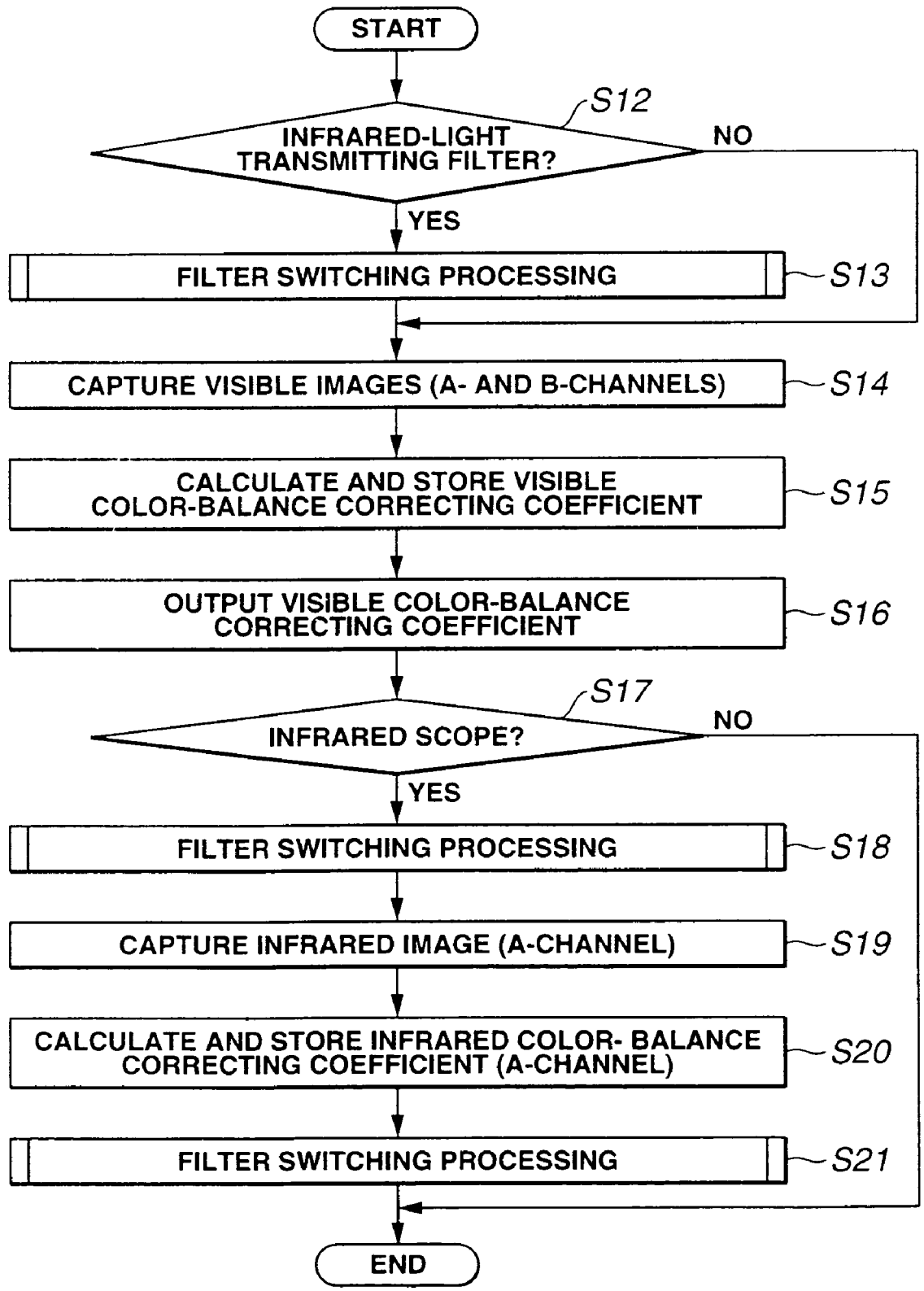
FIG. 15 is a flowchart for explaining the flow of color balance setting processing.

Referring to FIG. 15, in step S12, it is confirmed whether or not the infrared light transmitting filter 36 is inserted in the optical path. If it is confirmed that the infrared light transmitting filter 36 is inserted in the optical path, the processing sequence shifts to step S13. If it is confirmed that the infrared light transmitting filter 36 is not inserted in the optical path, that is, the visible light transmitting filter 35 is inserted in the optical path, the processing sequence shifts to step S14.

The filter switching processing (processing sequence in FIG. 14) is executed in step S13, thereby inserting the visible light transmitting filter 35 in the optical path. Then, the processing sequence shifts to step S14.

In step S14, the CPU 31 captures the visible image signals of the A- and B-channels after A/D conversion. After that, the processing sequence shifts to step S15.

In step S15, the visible color balance correcting coefficients for A- and B-channels are calculated so as to set, to predetermined values, the brightness ratios of the respective images of the respective signals R, G, and B of the A- and B-channels, and so as to correct the variation such as the amplifying ratios between the A- and B-channels. The resultant coefficients are stored in the memory of the CPU 31. Then, the processing sequence shifts to step S16.

In step S16, the CPU 31 stores, the color balance correcting coefficients for visible image calculated in the processing in step S15 are stored into the color balance correcting coefficient storing memories 43r, 43g, and 43b. Then, the processing sequence shifts to step S17.

In step S17, it is determined that the connected scope 2 is the infrared scope. If it is determined that the scope 2 is not the infrared scope, the series of processing ends. If it is determined that the scope 2 is the infrared scope, the processing sequence shifts to step S18.

In step S18, the filter switching processing (sequence in FIG. 14) is executed and the infrared light transmitting filter 36 is inserted into the optical path. Then, the processing sequence shifts to step S19.

In step S19, the CPU 31 captures the infrared image of the A-channel. After that, the processing sequence shifts to step S20.

In step S20, the color balance correcting coefficient for the infrared light of the A-channel is calculated so as to set, to predetermined values, brightness ratios of the infrared images picked-up at the timing for inserting the R-filter 37, G-filter 38, and B-filter 39 in the optical path. The resultant coefficient is stored in the memory of the CPU 31. After that, the processing sequence shifts to step S21.

In step S21, the filter switching processing (processing sequence in FIG. 14) is executed and the visible light transmitting filter 35 is inserted in the visible light transmitting filter 35, thereby switching the image to the visible image. Then, the series of processing ends.

Only by pressing the color balance setting switch 32, the color balance correction for the visible light and the color balance correction for the infrared light are easily set.

Figure 16:
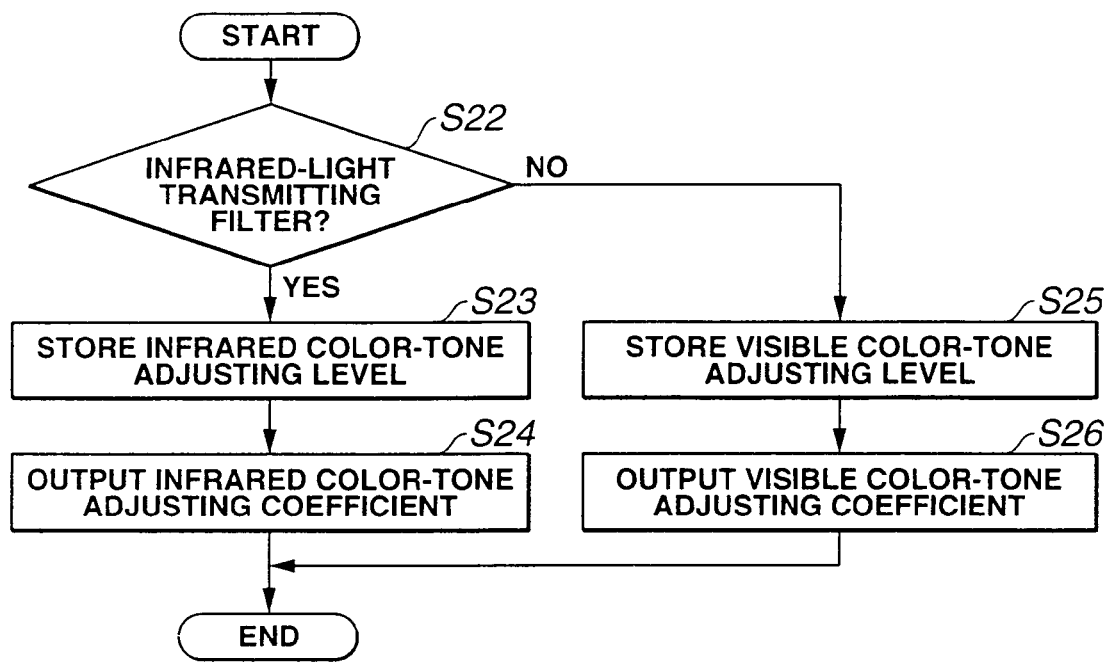
FIG. 16 is a flowchart for explaining color-tone setting processing.

Hereinbelow, a description is given of the operation upon changing the color-tone level by using the color-tone setting switch 34 with reference to the flowchart in FIG. 16.

The user changes the color-tone level by using the color-tone setting switch 34. Then, the color-tone setting requesting signal is transmitted to the CPU 31. The color-tone setting requesting signal includes information indicating any of the signals R, G, and B is set to which level. The CPU 31 detects the color-tone setting requesting signal and then executes the flowchart shown in FIG. 16, namely, the processing sequence of the color-tone setting processing.

In step S22, it is confirmed whether or not the infrared light transmitting filter 36 is inserted in the optical path. If it is confirmed that the filter inserted in the optical path is the infrared light transmitting filter 36, the processing sequence shifts to step S23. If it is confirmed that the filter inserted in the optical path is not the infrared light transmitting filter 36, that is, the visible light transmitting filter 35 is inserted in the optical path, the processing sequence shifts to step S25.

In step S23, the changed setting value is stored in the memory of the CPU 31 as the infrared color-tone adjusting level. Then, the processing sequence shifts to step S24.

In step S24, the color-tone adjusting coefficients of the signals R, G, and B corresponding to the changed levels are stored in the color-tone adjusting coefficient storing memories 53r, 53g, and 53b. After that, the series of processing ends.

It is determined in step S22 that the visible light transmitting filter 35 is inserted in the optical path and then the processing sequence shifts to step S25. In step S25, the input set value is stored in the memory of the CPU 31 as the visible color-tone adjusting level. After that, the processing sequence shifts to step S26.

In step S26, the color-tone adjusting coefficients of the signals R, G, and B corresponding to the changed levels are stored in the color-tone adjusting coefficient storing memories 53r, 53g, and 53b. Thereafter, the series of processing ends.

The color-tone setting switch 34 is one switch functioning as a switch for the visible image and a switch for the infrared image, which changes the color-tone adjusting level corresponding to the inserted filter.

The user changes the set value of the image processing (emphasizing level for image emphasis) by using the image processing setting switch 33. Then, an image processing setting requesting signal is transmitted to the CPU 31. The CPU 31 receives the image processing setting requesting signal. Similarly to the case of changing the color-tone level, the changed infrared or visible image emphasizing level (including color-tone emphasizing level and structure emphasizing level) is stored in the memory of the CPU 31. Then, the changed emphasizing level is transmitted to the image processing circuit.

As mentioned above, the image processing setting switch 33 is one switch functioning as a switch for the visible image and a switch for the infrared image, which changes the image emphasizing level corresponding to the inserted filter.

Figure 17:
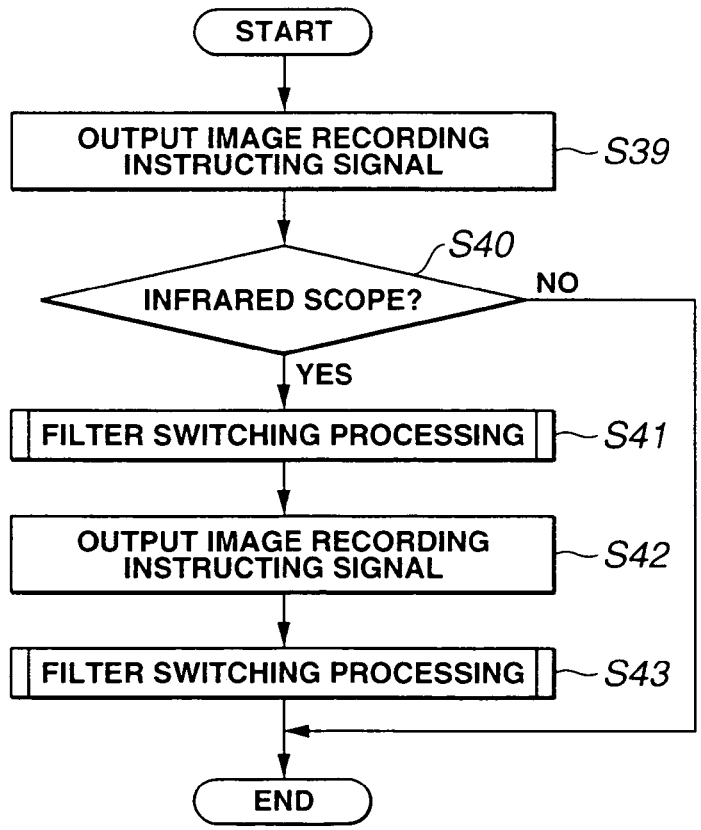
FIG. 17 is a flowchart for explaining the flow of image recording processing.

Hereinbelow, a description is given of the operation when the user presses the release switch 17 and the image is recorded with reference to the flowchart of FIG. 17.

The user presses the release switch 17 and then an image recording requesting signal is transmitted to the CPU 31. The CPU 31 receives the image recording requesting signal and then executes the flowchart shown in FIG. 17, namely, the processing sequence of the image recording processing.

In step S39, an image recording instructing signal is transmitted to the image recording devices (digital filing device 5 and photographing device 6). Then, the processing sequence shifts to step S40.

The image recording devices start executing the sequence for the image recording sequence in response to the image recording instructing signal. In this case, the digital filing device 5 communicates with the processor 3, thus to receive information such as the set values of the color-tone adjustment and the image processing, the type of the inserted filter, the type of scope, and patient data, and records the received information as header information of the recorded image, together with the image.

In step S40, the determining processing is executed whether or not the connected scope 2 is the infrared scope. If it is determined that the connected scope 2 is not the infrared scope, the series of processing ends.

If it is determined in step S40 that the connected scope 2 is the infrared scope, the processing sequence shifts to step S41.

In step S41, the filter switching processing (sequence in FIG. 14) is executed. Then, the processing sequence shifts to step S42.

In step S42, the image recording instructing signal is transmitted to the image recording device again. After that, the processing sequence shifts to step S43.

In step S43, the filter switching processing (processing sequence in FIG. 14) is executed. Thus, the filter state is returned to the original state. After that, the series of processing ends.

By executing the above processing, the user presses the release switch 17 only once, thus to record both the visible image and the infrared image.

According to the embodiment, upon infrared-light observation, the monitor 4 displays the wavelength of 805 nm as the R- and G-components and the wavelength of 930 nm as the B-component. The graph of FIG. 18 indicates the transparency of the ICG. Referring to the graph of FIG. 18, the abscissa denotes the wavelength and the ordinate denotes the transmittance. When the wavelength has the low transmittance, the ICG greatly absorbs the light. In the case of using the single ICG, the wavelength having the largest absorption (the lowest transmittance) is slightly shorter than 800 nm. However, in the case of the ICG administered in the living body, the wavelength having the lowest transmittance slightly shifts to a longer wavelength side due to the influence of the combination with the protein. The effective maximum absorbing wavelength of the ICG is approximately 805 nm within the range from the visible area to the near infrared area.

Figure 18:
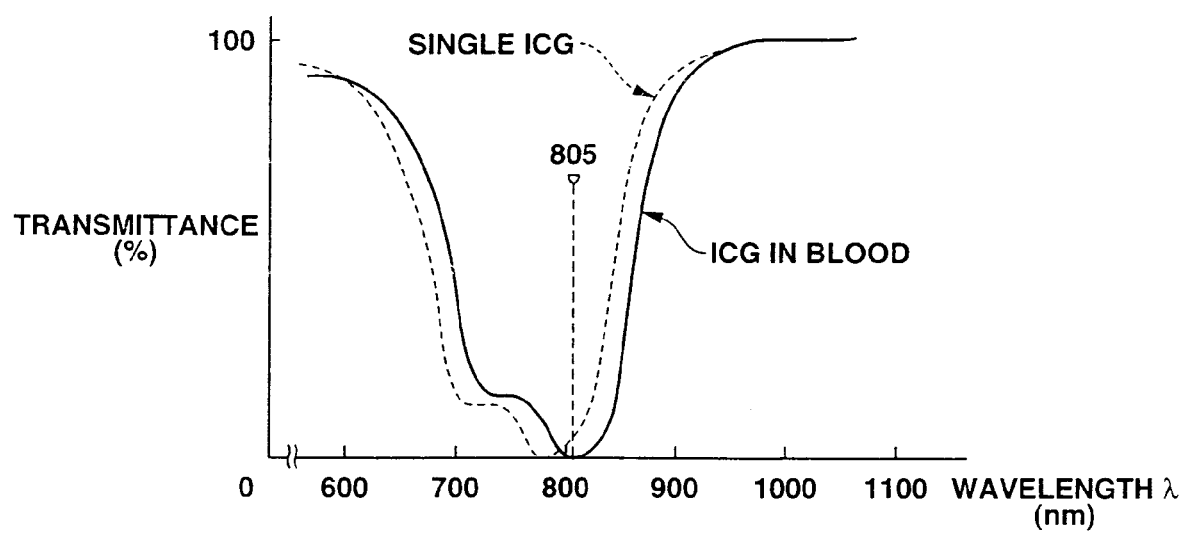
FIG. 18 is a diagram showing the transparency of the ICG.

Referring to FIG. 18, the ICG absorbs the small amount of light having the wavelength of 930 nm. Therefore, if the ICG is injected to the vein, the image of the wavelength of 805 nm has a dark blood-vessel portion and high contrast with the light being absorbed by the ICG. On the contrary, in the case of the image with the wavelength of 930 nm, the ICG absorbs the small amount of light, the blood vessel portion is not so dark, and therefore the image has low contrast.

The wavelength of 805 nm is allocated to the G- and R-components of the monitor 4. The wavelength of 930 nm is allocated to the B-component of the monitor 4. Thus, as the ICG absorbing result, the image having the blood vessel portion which is dyed in blue is observed on the monitor 4.

A relatively fine portion of the blood vessel portion is observed with the high contrast in the normal endoscope image, namely, visible image. Because the hemoglobin as the pigment in the living body has characteristics for absorbing the large amount of light of the blue and green wavelengths and the change in luminance of the obtained image is relatively large.

According to the embodiment, the endoscope apparatus of the field-sequential system is applied. Further, a mosaic filter of a simultaneous-system endoscope apparatus has infrared transparency and, thus, the same advantages as those according to the embodiment is obtained.

The technology for changing the various set values in accordance with the switching of filters is not limited to the switching of the infrared light transmitting filter and the visible light transmitting filter according to the embodiment. Further, the technology may be applied to the switching of a plurality of visible light having varied characteristics, such as ultraviolet light or fluorescent light.

Upon switching the filters, means for recognizing the type of filter that is currently inserted in the optical path may automatically recognize based on the image quality whether the image is the infrared one or the visible one.

In place of the color-tone adjusting circuit 26, the CPU 31 multiplies the color balance correcting coefficient and the color-tone adjusting coefficient. The resultant product is stored in the color balance correcting coefficient storing memory and thus the color balance correcting circuit 22 may also function as the color-tone adjusting circuit. Advantageously, the structure contributes to the reduction in manufacturing costs.

The pigment amount calculating circuit 46 of the image processing circuit 25 obtains the luminance value of the image, in place of the ICG amount upon inserting the infrared light transmitting filter 36, and the pigment emphasizing circuit 49 converts the contrast based on the average luminance value of the image. Thus, the contrast of the infrared image may be adjusted and be observed.

The image processing circuit 25 is not limited to the image processing circuit which is incorporated in the processor 3 according to the embodiment. The image processing circuit 25 may be an external device or may transmit the image signal or control signal via a cable.

Further, in the halfway of processing, a luminance signal and a color signal are formed from the signals R, G, and B, and the image signal may be outputted as a composite signal from the processor 3 and may be inputted to the monitor 4.

The monitor 4 is not limited to the CRT-system monitor and may be a plasma display device or a liquid crystal device.

Whether or not the light source corresponds to the infrared observation may be determined by the communication between the CPU 31 in the processor 3 and the light source device 7, thus to perform the branching processing similarly to the determination of the infrared scope according to the embodiment.

The filter selection switch 16 is arranged to the front panel of the light source device 7 and the communication is established between the light source device 7 and the CPU 31 of the processor 3, thereby requesting the filter switching. Thus, the same processing as that according to the embodiment may be performed.

Hereinbelow, a detailed description is given of use of methods adopting the infrared observing system with the above-mentioned structure.

The use of method of the infrared observing system in the thoracoscope is as follows upon observing the emphysematous lesions of the lung.

That is, in the pneumothorax operation, the radical cure is established by resecting and suturing the bulla as the localized pneumothorax lesions of the lung as the source. However, it is reported that a recurrence rate of emphysematous after the thoracoscopic operation is about several to ten times of that of the direct operation with the thoracotomy. This is caused by the mistake of emphysematous lesions as the pneumothorax source or the incomplete removal thereof. Therefore, the thoracoscopic operation needs to identify the accurate emphysematous lesions (Bulla) during the operation. Further, the recurrence rate after the thoracoscopic radical-cure operation of pneumothorax is reduced by preventing the mistake of emphysematous lesion and incomplete removal.

Figure 19:
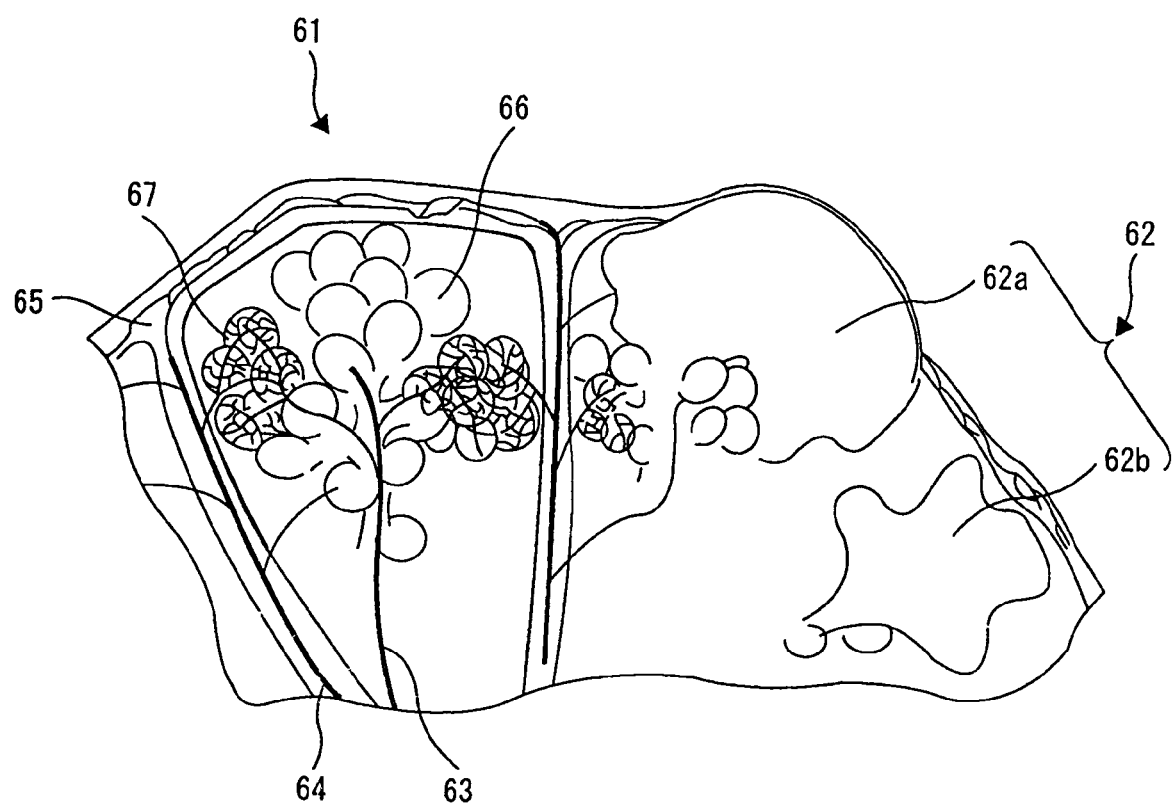
FIG. 19 is an enlarged schematic diagram enlarging and showing a part of the pulmonary tissue and conceptually showing the portion of the normal lung and the portion in the emphysema.

FIG. 19 is an enlarged schematic diagram of a main portion, enlarging and showing a part of the pulmonary tissue and conceptually showing the portion of the normal lung and the portion in the emphysematous change.

In the normal case, a normal lung 61 has a high density of the tissue and rich bloodflow on the lung surface. The bloodflow is coarse at portions (referred to as emphysematous lungs) 62a and 62b having the emphysematous change. Further, the bloodflow does not exist in the bullas 62a and 62b and therefore, even if the bloodflow and the ICG together is visualized, the ICG color is not visualized at the portion of the emphysematous lung 62 as the source of pneumothorax.

In this case, since the infrared light used as the observing light has high tissue transparency, the bloodflow at the portion deeper than the lung surface is visualized, as compared with the conventional visible-light observation.

Figure 20:
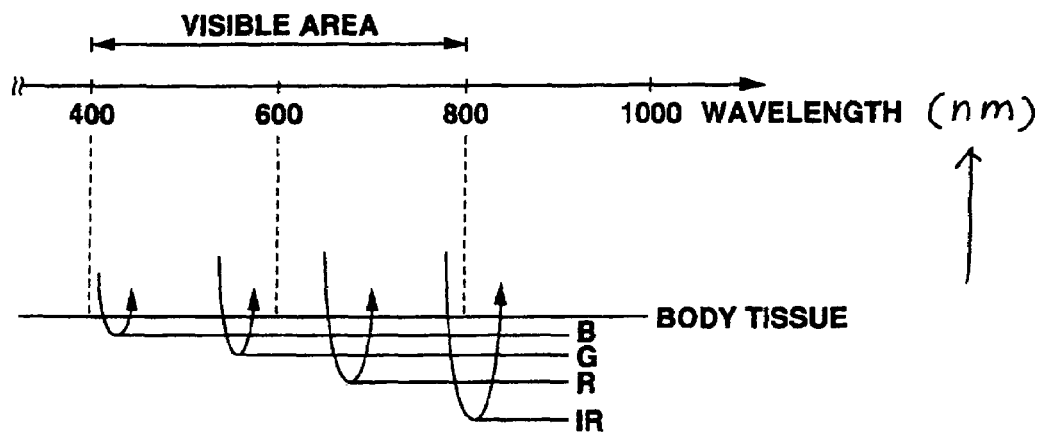
FIG. 20 is a schematic diagram showing a relationship between the light wavelength and the observing depth.

FIG. 20 is a schematic diagram showing a relationship between the light wavelength and the observing depth. Referring to FIG. 20, the infrared light (IR) has the high tissue-transparency as compared with those of the visible wavelengths (B, G, and R) and reaches the portion deeper than that of the visible wavelength.

Thus, by using the infrared light (IR), it is possible to visualize, as the image, even the fine bulla 62b (refer to FIG. 19). submerging on the bottom of the lung surface, which is not visualized by the normal light (visible light; wavelengths R, G, and B in the visible area).

Referring to FIG. 19, reference numeral 63 denotes an artery, reference numeral 64 denotes a vein, reference numeral 65 denotes a pleura, reference numeral 66 denotes a pulmonary alveolus, and reference numeral 67 denotes a capillary plexus.

Based on the result of the basic research, obviously, it is pathologically proved that the portion having the emphysematous change as compared with the normal portion is visualized with the time delay of ten-odd to several tens seconds by using the ICG.

Figure 21A:
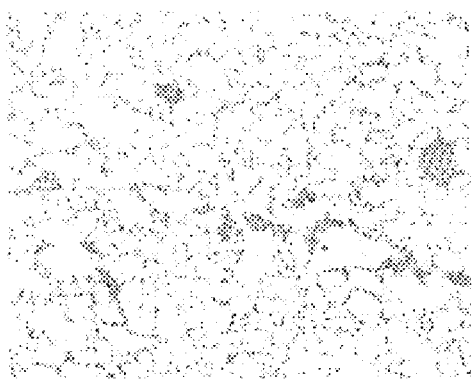
FIGS. 21A to 21D are showing a pulmonary emphysema model and an image of the normal portion of the pulmonary tissue which are artificially formed.
Figure 21B:
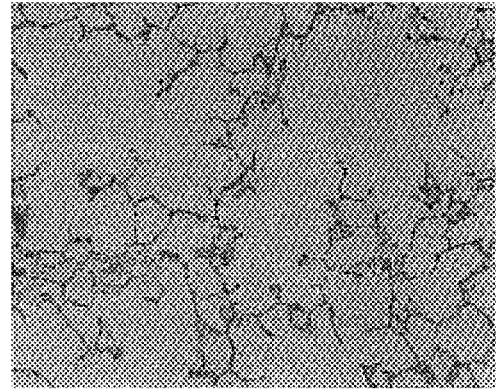
Figure 21C:
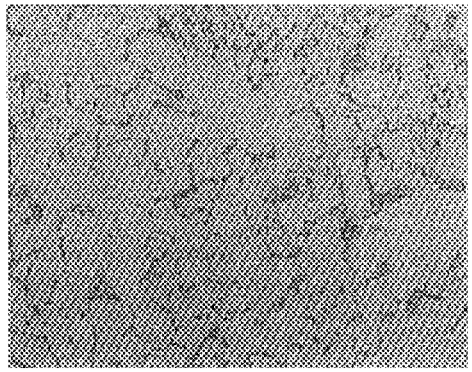
Figure 21D:
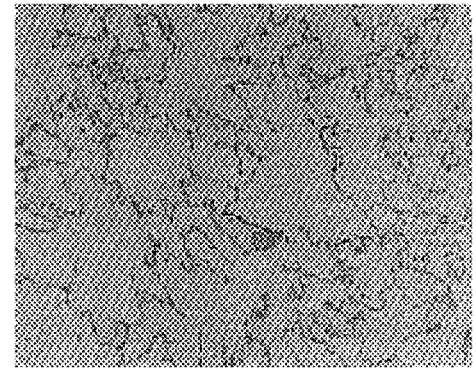

FIGS. 21A to 21D show an image of the normal portion of the pulmonary tissue and a pulmonary emphysema model which is artificially formed by injecting, to a dog, the enzyme that is called PPE (Porcine Pancreatic Elastase). FIG. 21A shows the image of the normal tissue. FIG. 21B shows the image of the pulmonary tissue after zero day of the PPE injection. FIG. 21C shows the image of the pulmonary tissue after eighteen days of the PPE injection. FIG. 21D shows the image of the pulmonary tissue after thirty-three days of the PPE injection. FIG. 21A further shows the image magnified forty times. FIGS. 21B to 21D further show the image magnified one hundred times.

After injecting the ICG to the vein in the pulmonary tissue, the tissue images (refer to FIGS. 21B to 21D) of the area having the ICG visualized with the delay of 15 sec under the two-wavelength infrared light observation includes the tissue image of the emphysema which causes the destroy of the pulmonary alveolus structure, different from the normal tissue (refer to FIG. 21A).

Further, in accordance with the aging, the dust deposition is recognized in the lung. Thus, using the infrared light having a plurality of wavelengths in the thoracoscopic observation, the bulla is clearly visualized without the influence of dusts by allocating the bloodflow information to a pseudo color. In the case of the infrared light having a single wavelength, a monochrome image is obtained and therefore the dusts are not distinguished from the normal lung or the contrast of the emphysematous lung.

Figure 22:
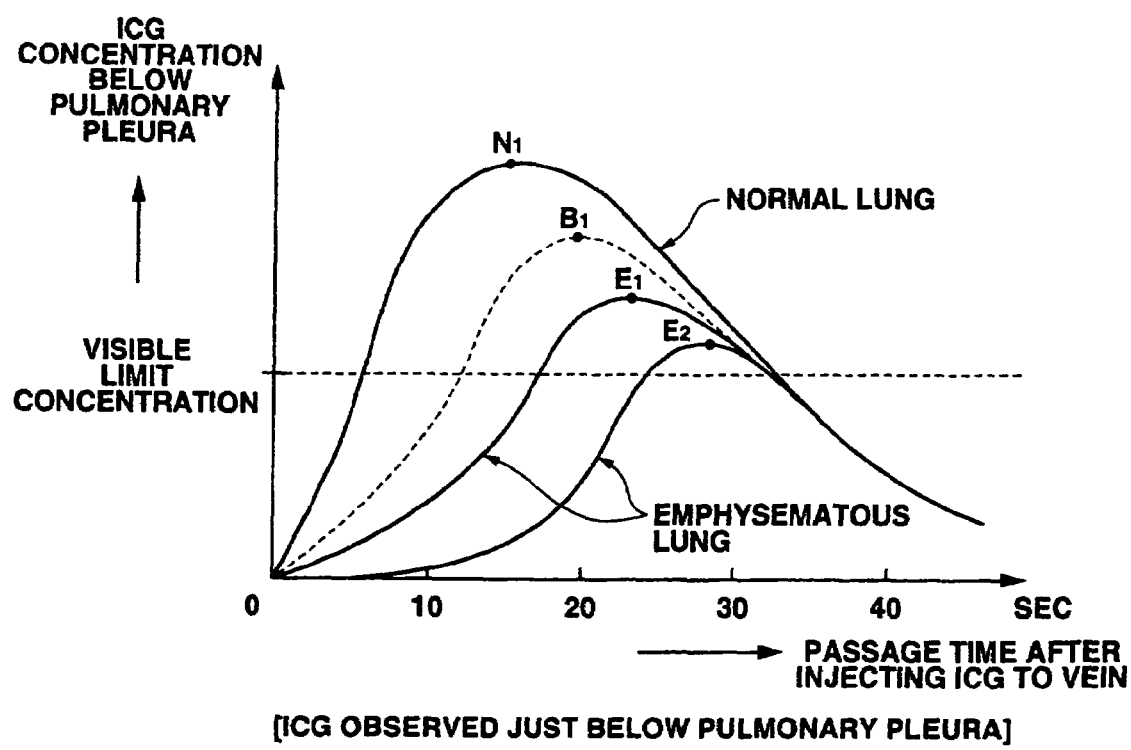
FIG. 22 is a graph showing a relationship between the passage of time after ICG venous injection and the ICG concentration.

FIG. 22 is a graph showing the relation between the passage of time after ICG venous injection and the ICG concentration observed just below the pulmonary pleura.

Four curves denote, in order of the higher peaks, typical normal lung (shown by a solid line), lung at the boundary between the normal lung and the emphysematous lung (shown by a broken line), and two examples of the typical emphysematous lung (shown by solid lines). Further, the four curves denote ICG pigment maximum values (N1, B1, E1, and E2) which are visualized at the portions.

As the time to visualize the ICG is longer, this indicates the advanced emphysema portion which requires much time to the visualization.

Therefore, the infrared-light observation enables the determination of the emphysematous lung and the normal lung with the time delay before the ICG visualization of the lung surface. Alternatively, in the portion having the remarkable emphysematous degree, the maximum value of the pigment is less than the visualization limit concentration. In this case, it is only determined based on the presence or absence of ICG visualization whether the lung is the emphysematous lung or the normal lung.

The infrared-light observation is not limited to that using the endoscope (laparoscope or thoracoscope) and can easily be applied to an image pick-up system used in the celiotomy or thoracotomy.

Hereinbelow, a description is given of a specific use of the above-mentioned infrared observing system when applied on the thoracoscopic operation for the emphysematous lung and the pneumothorax.

(1) The patient takes the lateral position while the single lung-ventilation is used under the general anesthesia and the affected part is directed upward.

(2) The light source device 7 and processor 3 in the infrared observing system (refer to FIG. 1) and another peripheral device are turned on (ON-state).

(3) A lamp switch (not shown) of the light source device 7 is turned on and then the white balance is adjusted in the normal observing mode (visible-light observing mode).

(4) Similarly to the general thoracoscopic operation, the necessary number of resecting portions connecting the extra-body and the thoracic cavity, and trocar, namely, a guide tube having the diameter of φ5 to φ10 mm is indwelled at the intercostals.

(5) The scope is inserted in the thoracic cavity. In the normal observing mode (visible-light observing mode), the thoracic cavity is observed. Thus, the position of bulla and the observing target range are confirmed.

(6) The scope (therapeutic instrument) is pulled out as needed. Air is fed to the lung having the affected part, which is deaired, via a trachea tube by a proper pressure. Thus, the entire lung is expanded.

(7) After that, the inner pressure of the bronchi on the affected side is released to an atmospheric pressure, that is, the lung is deflated. Then, the thoracoscope is inserted in the thoracic cavity again. At a period from this time point to the following steps sequent to step (10), the touching of the lung parenchyma is prevented.

The lung which is not pneumatized, namely, the atelectasis has the high density of the tissue and therefore the blood vessels thickly exist. In the observation of the thoracic cavity, if the lung parenchyma is touched, the touched portion is different from the non-touched portion, depending on the pnuematization or non-pnuematization. In the infrared-light observation, the detection of ICG concentration is not accurate. Therefore, after expanding the entire lung of the patient, preferably, the lung is deaired, that is, the inner pressure of the bronchi is released to the atmospheric pressure.

Figure 25:
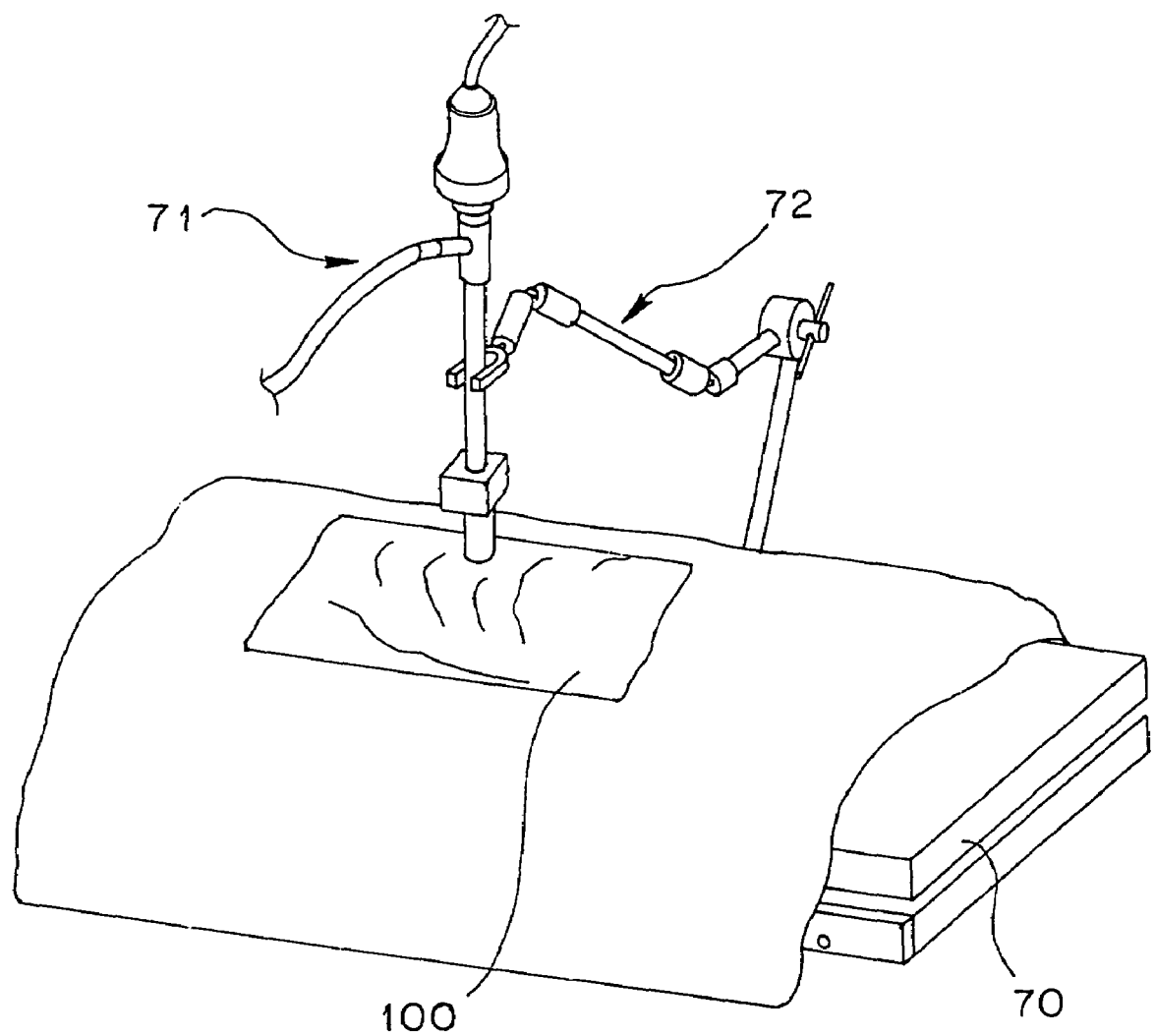
FIG. 25 is a diagram showing one example of means which fixes the observing range and showing a scope holder which is connected and fixed to an operation bed and holds and fixes a part of the observing apparatus (thoracoscope) in the thoracoscopic operation using the infrared observing system.

(8) The observing apparatus confirms the observing range. The mode is switched to the infrared-light observing mode and the observing range is fixed. In the fixing in this case, referring to FIG. 25, a scope holder 72 or a staff of the operation may hold a part of a thoracoscope 71, serving as the observing apparatus, connected and fixed to an operation bed 70 on which a patient 100 is laid.

(9) The ICG is administered in the vein of the patient.

The dose into the vein in this case is 0.5 to 5 mg/kg of weight of the patient. The ICG is administered as much as possible (within ten sec) via the vein line that is previously indwelled.

(10) The display device (monitor 4) in the observing apparatus confirms the range within which the ICG is visualized, the range within which the ICG is not visualized, and the range within which the ICG is visualized with the time delay.

Figure 23:
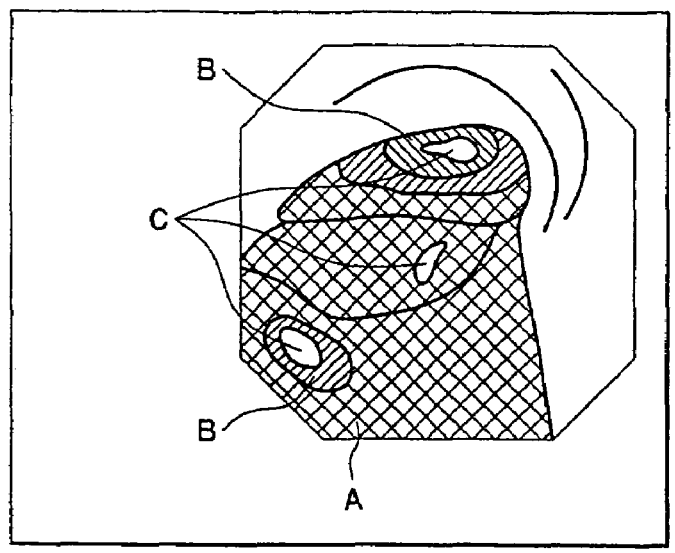
FIG. 23 is a diagram showing an example of a display image displayed in steps after ICG administration, in the thoracoscopic operation of the pulmonary emphysema and the pneumothorax using the above-mentioned infrared observing system.

FIG. 23 is a diagram showing a display example of the display screen of the monitor 4 in this step. Referring to FIG.

23, an area shown by reference symbol A denotes the range within which the ICG is visualized, an area shown by reference symbol B denotes the range within which the ICG is visualized with the time delay, and reference symbol C denotes the range within which the ICG is not visualized.

The marking treatment is performed by using a proper tool such as an electric knife and clip as needed.

The marking treatment uses an energy therapeutic instrument for the thoracoscope using the high frequency, ultrasonic waves, heat or the like. In place of the marking treatment, a suture needle or a clip may be used.

Figure 24:
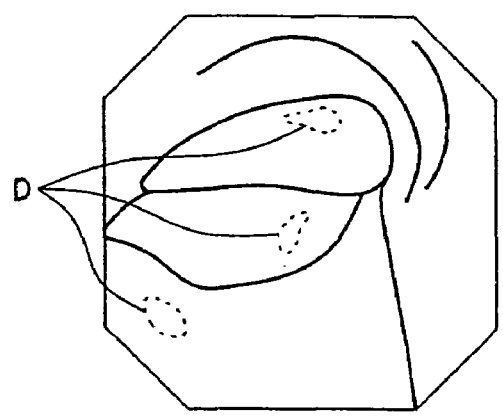
FIG. 24 is a diagram showing a marking state at the position near the lesion portion for the pulmonary emphysema and the pneumothorax in the thoracoscopic operation using the infrared observing system.

FIG. 24 is a diagram showing a marking state using the electric knife at the position near the lesion portion corresponding to the observing range in the step (display screen of the monitor 4 in FIG. 23). Referring to FIG. 24, a portion shown by reference symbol D denotes a marking portion.

(11) After switching the infrared observing mode to the normal observing mode, the incision operation is performed to the range within which the ICG is not visualized or to the range (marking range) within which the ICG is visualized with time delay, and the corresponding portion is removed. Then, the incision portion is sutured by using predetermined suturing means. The suturing means used in this case is preferably an automatic suture machine. However, if the incision portion is minute, it is subjected to the reefing by a high frequency electric knife, an ultrasonic coagulating device, or an energy curing device such as a laser knife.

(12) The operation steps sequential to step (6) or operation steps sequential to step (9) are repeated if needed. During the removal using the automatic suturing machine, the mode may be switched to the infrared observing mode so as to confirm a next incision scheduled line.

(13) After completing the treatment for the emphysematous lesion, a leak test, namely, a test for confirming the presence or absence of leak is executed by applying the inner pressure to the bronchi after filling the thoracic cavity with physiological saline.

Hereinbelow, a description is given of a method to use the infrared observing system for observing with the laparoscope the mesentery of the mesenteric artery embolism.

The mesenteric artery occlusion that is affected after the operation is an excessively poor-prognosis disease that the necrosis of the intestinal tract is caused by choking the small thrombus in the many-branched fine mesenteric artery in many cases. The cure or operation method is generally as follows.

That is, under the celiotomy, the thrombus position is determined by touching the thrombus of the mesenteric artery. After the removal operation of the thrombus of the thick artery with the diameter having 5 mm that is branched from the abdomen aorta, the intestinal tract in necrosis is removed.

However, the mesenteric artery draws the loop at the periphery thereof and, even if it is choked at one portion, the bloodflow enters from the choking portion and the necrosis is prevented. Currently, the necrosis degree of the intestinal tract tissue is estimated based on the color-tone change of the serosal surface of the intestinal tract, and it is determined whether the color-tone change is the reversible change or the irreversible change, and the removal portion of the intestinal tract is determined.

When the accurate determination is impossible, the harmful influence is affected to the digestion and absorption function due to the overcut of intestinal tract. On the contrary, when the necrosis portion irreversibly remains, the intestinal tract is perforated after the operation and the peritonitis is accompanied.

In the above infrared observing system, the bloodflow distribution of tissue is visualized, thereby performing the proper incision operation. In this case, the mesenteric artery and vein or the serosal surface side of the front wall of the intestinal tract, to which bloodflow flows, are mainly observed. The observation is not limited to that using the laparoscope and may be performed under the celiotomy.

Hereinbelow, a description is given of a specific method of using the laparoscope which uses the infrared observing system for the mesentery of the mesenteric artery embolism.

(1) The patient is under the general anesthesia and is subjected to the observation and treatment under the celiotomy or by using the laparoscope.

(2) The light source device 7 and processor 3 in the infrared observing system (refer to FIG. 1) and peripheral devices are turned on (ON-state).

(3) A lamp switch (not shown) of the light source device 7 is turned on and then the white balance is adjusted in the normal observing mode (visible-light observing mode).

(4) In the operation using the laparoscope, the necessary number of resecting portions for connecting the extra-body and the abdominal cavity, and trocar, namely, a guide tube having the diameter of $\phi 5$ to $\phi 10$ mm is indwelled at the abdominal wall. After that, the treatment for insufflation of the abdominal cavity for ensuring the operation space is performed by feeding $CO_2$ into the abdominal cavity.

(5) The scope and the therapeutic instrument are inserted in the abdominal cavity. The abdominal cavity is examined in the normal observing mode (visible-light observing mode).

(6) After switching the observing apparatus to the infrared observing mode, the ICG is administered to the vein of the patient. The dose of ICG into the vein in this case is 0.5 to 5 mg/kg per weight of the patient. The ICG is administered as much as possible (within ten sec) via the vein line that is previously indwelled.

(7) The serosal surface of the front wall of the intestinal tract is observed by developing the mesentery with the therapeutic instrument. Determined is the range within which the ICG is visualized, the range within which the ICG is not visualized, and the range within which the ICG is visualized with the time delay. The marking treatment is performed as needed. The ischemic portion is identified by the operation step.

(8) Further, the artery flowed to the ischemic portion is identified.

(9) After switching the infrared observing mode to the normal observing mode, the thrombus of the artery flowed to the ischemic portion is removed. Further, the ischemic portion of the intestinal tract is removed.

(10) The operation steps sequential to step (6) is repeated as needed. Thus, it is confirmed that the ischemic portion does not exist (operation effect is evaluated).

Hereinbelow, a description is given of a method to use the infrared observing system upon observing the coronary artery of the myocardial infarction and the angina pectoris with the thoracoscope.

The myocardial infarction and the angina pectoris correspond to a state in which the bloodflow stops or lacks due to the occlusion or stricture of the coronary artery as the nutritional blood vessel of the heart. The surgery uses the aorta or internal thoracic artery and executes the bypass to the periphery of the choked coronary artery. In this case, the bypass portion is determined by a result of the angiography examination before the operation and the degree of the arteriosclerosis of the portion. Further, after the bypass operation, the bloodflow rate of the bypass is measured by an electromagnetic flowmeter or a Doppler rheometer and the resumption of bloodflow is checked.

Upon determining the bypass portion, the bloodflow rate of the tissue (heart) is grasped during the operation by the infrared observing system. Thus, the function of the tissue can be evaluated different from the case of the conventional determination using only the state of the coronary artery. The bypass portion is accurately determined.

Further, the improvement of the bloodflow of the tissue after the bypass can be evaluated as the image during the operation, and the evaluation of the operation is improved. The observation is not limited to the laparoscope and may be performed under the celiotomy.

Hereinbelow, a description is given of a specific using method of the thoracoscope as an auxiliary tool using the infrared observing system for the myocardial infarction and the angina pectoris.

(1) The patient is under the general anesthesia and is subjected to the observing treatment under the celiotomy or by using the laparoscope.

(2) The light source device 7 and processor 3 in the infrared observing system (refer to FIG. 1) and peripheral devices are turned on (ON-state).

(3) A lamp switch (not shown) of the light source device 7 is turned on and then the white balance is adjusted in the normal observing mode (visible-light observing mode).

(4) In the operation using the thoracoscope, the necessary number of resecting portions for connecting the extra-body and the thoracic cavity, and trocar, namely, a guide tube having the diameter of $\phi 5$ to $\phi 10$ mm is indwelled at the thoracic wall.

(5) The scope and the therapeutic instrument are inserted in the thoracic cavity. The thoracic cavity is observed in the normal observing mode (visible-light observing mode).

(6) After switching the observing apparatus to the infrared observing mode, the ICG is administered to the vein of the patient. The ICG dose in the vein in this case is 0.5 to 5 mg/kg of weight of the patient. The ICG is administered as much as possible (within ten sec) via the vein line that is previously indwelled.

(7) The heart surface is observed so as to confirm the portion at which the ICG is not visualized or the portion at which the ICG is visualized with the time delay, namely, ischemic range. The bypass portion is determined by comparison with the evaluation before the operation.

(8) The artificial heart and lung are attached so as to perform the bypass operation. Under the thoracoscopic observation, the bypass operation is performed after switching the infrared observing mode to the normal observing mode. Under the thoracotomy, the bypass operation is performed by direct viewing.

(9) The artificial heart and lung are detached, and the improvement of the tissue bloodflow rate of the ischemic portion is evaluated again by the steps succeeding step (6) before the resumption operation of the bypass bloodflow.

Further, the thoracoscope using the infrared observing system can be applied to another disease as uneven distribution of the bloodflow, e.g., the neoplastic lesion including the liver tumor, lymphoreticular-tissue tumor, nephroma, pancreatic tumor, or adrenal tumor.

The tumor generally generates new tumor blood vessel and has a rich bloodflow as compared with the normal tissue. Thus, the infrared observing system observes the thoracic cavity or abdomincal cavity, thereby confirming the spread of the tumor in realtime. Further, information important to the operation is provided.

As mentioned above, according to the embodiment, the infrared observing system comprises the light source device which radiates the light of the first wavelength band including the wavelength of 805 nm and the light of the second wavelength band including the wavelength longer than 805 nm. Further, the color components indicated by the images of the first and second wavelength bands of the object irradiated by the light radiated from the light source device are allocated to the red, green, and blue. The ICG (infrared absorbing pigment) is picked up by the light of the second wavelength band, and is displayed with the allocated color component. Thus, the bloodflow (blood vessel run) of the deep portion which is not visualized by the normal light (visible light) is displayed and identified with the color component of the red, blue, and green by visualizing the ICG.

In the disease having the bloodflow of the-organ different from that of the normal tissue, such as the ischemic disease, the ICG is administered into the vein and then the portion having a rich bloodflow absorbs the light of the first wavelength band (805 nm) and reflects only the light of the second wavelength band longer than the first one. Thus, the color allocated to the second wavelength band is promptly visualized after injecting the ICG to the vein. In the meantime, the portion having a shortage of bloodflow reflects the light of the first and second wavelength bands until at least the passage of a certain time after the ICG is administered to the vein. Consequently, the color is visualized as white during the light reflection of the first and second wavelength bands.

As mentioned above, the information on the time delay before visualizing the color information of the image or the like is obtained in realtime during the operation. The information facilitates the identification of the ischemic portion.

For example, in the healthy lung having the rich bloodflow and the pulmonary emphysema which is vacuolar and which does not have the bloodflow, the pulmonary emphysema reflects the light of the first and second wavelength bands during a predetermined time after administering at least the ICG to the vein because of the shortage of bloodflow and thus it is visualized as white during it.

According to the present invention, the object to obtain the image information that is not obtained by the direct viewing is accomplished by using the wavelength in the near infrared area and the image pick-up device such as the CCD. Therefore, it is a matter of course that the present invention is not limited to the endoscopic operation.

The applying disease can be any disease having the difference in bloodflow between the normal portion and the lesion portion, such as the ischemic disease.

Thus, it is possible to provide the infrared observing system which easily and accurately determines the treatment target portion by paying attention to the organ surface and by visualizing in realtime the bloodflow distribution, which properly cures the determined portion, and which easily confirms the best curing advantage.

Having described the preferred embodiments of the invention referring to the accompanying drawings, it should be understood that the present invention is not limited to the those precise embodiments and various changes and modifications thereof could be made by one skilled in the art without departing from the spirit or scope of the invention as defined in the appended claims.

What is claimed is:

1. A lesion portion determining method of an infrared observing system, the infrared observing system comprising at least an observing apparatus, the observing apparatus comprising:

a light source device which radiates light of a first wavelength band including a wavelength of 805 nm and light of a second wavelength band including a wavelength longer than 805 nm;

an image pick-up device which picks up an image of the first wavelength band and an image of the second wavelength band of the object irradiated by the light radiated from the light source device;

display means which displays, as any color component of red, green, and blue, the image of the first wavelength band and the image of the second wavelength band that are picked-up by the image pick-up device;

the lesion portion determining method comprising:

a step of administering an infrared absorbing pigment to a patient;

a step of observing a visible range of the infrared absorbing pigment by the observing apparatus;

a step of distinguishing a bloodflow state of a tissue depending on the visualizing difference in the infrared absorbing pigment that is observed by the observing apparatus; and a step of distinguishing the bloodflow state of the tissue based on the time until visualizing the infrared absorbing pigment.

2. The lesion portion determining method of an infrared observing system according to claim 1, wherein the infrared absorbing pigment is administered in the vein of the patient.

3. The lesion portion determining method of an infrared observing system according to claim 1, further comprising: a step of distinguishing the bloodflow state of the tissue based on the presence or absence of visualization of the infrared absorbing pigment.

4. The lesion portion determining method of an infrared observing system according to claim 3, further comprising: a step of performing the treatment in accordance with the bloodflow state of the tissue.

5. The lesion portion determining method of an infrared observing system according to claim 4, further comprising: a step of marking an affected part in the treatment in accordance with the tissue state.

6. The lesion portion determining method of an infrared observing system according to claim 5, further comprising: a step of removing the marked portion.

7. The lesion portion determining method of an infrared observing system according to claim 5, further comprising: a step of improving the bloodflow state of the tissue.

8. The lesion portion determining method of an infrared observing system according to claim 7, further comprising: a step of bypassing the blood vessel in the treatment for improving the bloodflow state of the tissue.

9. The lesion portion determining method of an infrared observing system according to claim 4, further comprising: a step of repeating the treatment in accordance with the tissue state and the administration of the infrared absorbing pigment.

10. The lesion portion determining method of an infrared observing system according to claim 4, further comprising; a step of confirming a treatment result by administering the infrared absorbing pigment.

11. The lesion portion determining method of an infrared observing system according to claim 1, further comprising: a step of distinguishing the bloodflow state of the tissue based on the relative color contrast of the visualized infrared absorbing pigment.

12. The lesion portion determining method of an infrared observing system according to claim 11, further comprising: a step of performing the treatment in accordance with the bloodflow state of the tissue.

13. The lesion portion determining method of an infrared observing system according to claim 12, further comprising: a step of marking an affected part in the treatment in accordance with the tissue state.

14. The lesion portion determining method of an infrared observing system according to claim 13, further comprising: a step of removing the marked portion.

15. The lesion portion determining method of an infrared observing system according to claim 13, further comprising: a step of improving the bloodflow state of the tissue.

16. The lesion portion determining method of an infrared observing system according to claim 15, further comprising: a step of bypassing the blood vessel in the treatment for improving the bloodflow state of the tissue.

17. The lesion portion determining method of an infrared observing system according to claim 12, further comprising: a step of repeating the treatment in accordance with the tissue state and the administration of the infrared absorbing pigment.

18. The lesion portion determining method of an infrared observing system according to claim 12, further comprising: a step of confirming a treatment result by administering the infrared absorbing pigment.

19. The lesion portion determining method of an infrared observing system according to claim 1, further comprising: a step of performing a treatment based on the bloodflow state of the tissue.

20. The lesion portion determining method of an infrared observing system according to claim 19, further comprising: a step of marking an affected part in the treatment based on the bloodflow state of the tissue.

21. The lesion portion determining method of an infrared observing system according to claim 20, further comprising: a step of removing the marked portion.

22. The lesion portion determining method of an infrared observing system according to claim 20, further comprising: a step of improving the bloodflow state of the tissue.

23. The lesion portion determining method of an infrared observing system according to claim 22, further comprising: a step of bypassing the blood vessel in the treatment for improving the bloodflow state of the tissue.

24. The lesion portion determining method of an infrared observing system according to claim 19, further comprising: a step of repeating the treatment based on the bloodflow state of the tissue state and the administration of the infrared absorbing pigment.

25. The lesion portion determining method of an infrared observing system according to claim 19, further comprising: a step of confirming a treatment result by administering the infrared absorbing pigment.

26. The lesion portion determining method of an infrared observing system according to claim 1, further comprising: a step of guiding the observing apparatus to a target portion.

27. The lesion portion determining method of an infrared observing system according to claim 26, wherein the observing apparatus comprises optical means using visible light and infrared light, the lesion portion determining method further comprising: a step of fixing the observing apparatus for time-progress observation.

28. The lesion portion determining method of an infrared observing system according to claim 26, further comprising: a step of observing a thoracic cavity by the observing apparatus.

29. The lesion portion determining method of an infrared observing system according to claim 28, further comprising: a step of observing a lung by the observing apparatus.

30. The lesion portion determining method of an infrared observing system according to claim 29, further comprising: a step of expanding the lung.

31. The lesion portion determining method of an infrared observing system according to claim 30, further comprising: a step of blocking air flow in bronchi concerned with a target portion and expanding only a periphery side.

32. The lesion portion determining method of an infrared observing system according to claim 29, further comprising: a step of deairing the lung.

33. The lesion portion determining method of an infrared observing system according to claim 32, further comprising: a step of releasing a blocking of concerned bronchi to atmospheric pressure.

34. The lesion portion determining method of an infrared observing system according to claim 28, further comprising: a step of observing the heart by the observing apparatus.

35. The lesion portion determining method of an infrared observing system according to claim 26, further comprising: a step of observing the abdominal cavity by the observing apparatus.

36. The lesion portion determining method of an infrared observing system according to claim 35, further comprising: a step of observing the large intestine and the mesentery by the observing apparatus.

37. The lesion portion determining method of an infrared observing system according to claim 1, further comprising:
a step of guiding the observing apparatus to a target portion; and
a step of switching the observation using the visible light to the observation using the infrared light.

38. The lesion portion determining method of an infrared observing system according to claim 37, further comprising: a step of switching the observation using the visible light to the observation using the infrared light by an optical observing apparatus using the visible light and the infrared light.

39. The lesion portion determining method of an infrared observing system according to claim 37, further comprising: a step of switching the observation using the infrared light to the observation using the visible light.

40. The lesion portion determining method of an infrared observing system according to claim 39, further comprising: a step of switching the observation using the infrared light to the observation using the visible light by an optical observing apparatus using the visible light and the infrared light.

41. The lesion portion determining method of an infrared observing system according to claim 1, further comprising:
a step of guiding the observing apparatus to a target portion;
a step of performing a treatment based on the bloodflow state of a tissue; and
a step of switching the observation using the visible light to the observation using the infrared light.

42. The lesion portion determining method of an infrared observing system according to claim 41, further comprising: a step of switching the optical observation using the infrared light to the observation using the visible light.

* * * * *